(12) United States Patent
Martini et al.

(10) Patent No.: US 8,449,510 B2
(45) Date of Patent: May 28, 2013

(54) LID ASSEMBLY FOR A MEDICAL WASTE FLUID COLLECTION AND DISPOSAL SYSTEM

(75) Inventors: Anthony Martini, Olathe, KS (US); Lawrence Guerra, Mission, KS (US)

(73) Assignee: Dornoch Medical Systems, Inc., Riverside, MO (US)

( * ) Notice: Subject to any disclaimer, the term of this patent is extended or adjusted under 35 U.S.C. 154(b) by 137 days.

(21) Appl. No.: 13/188,058

(22) Filed: Jul. 21, 2011

(65) Prior Publication Data

US 2011/0278294 A1 Nov. 17, 2011

Related U.S. Application Data

(62) Division of application No. 12/245,966, filed on Oct. 6, 2008, now Pat. No. 8,292,857.

(60) Provisional application No. 60/997,787, filed on Oct. 4, 2007.

(51) Int. Cl.
*A61M 1/00* (2006.01)

(52) U.S. Cl.
USPC ............... 604/317; 604/27; 604/35; 604/48; 604/65; 604/118; 604/119; 604/318; 604/322; 604/326; 141/35; 141/59; 141/95; 141/198; 137/205

(58) Field of Classification Search
USPC .................................. 604/317, 318, 322, 326
See application file for complete search history.

(56) References Cited

U.S. PATENT DOCUMENTS

| | | |
|---|---|---|
| 2,275,472 A | 3/1942 | Samiran |
| 4,089,470 A | 5/1978 | Strahman |
| 4,354,571 A | 10/1982 | Lakin et al. |
| 5,266,233 A | 11/1993 | Houghton et al. |
| 5,280,963 A | 1/1994 | Schober et al. |
| 5,363,745 A | 11/1994 | Lin ................................ 99/306 |
| 5,723,870 A | 3/1998 | Crowne et al. ............... 250/577 |

(Continued)

OTHER PUBLICATIONS

The American Heritage® Dictionary of the English Language, Fourth Edition, 2000.

(Continued)

*Primary Examiner* — Tatyana Zalukaeva
*Assistant Examiner* — Ilya Treyger
(74) *Attorney, Agent, or Firm* — Seager, Tufte & Wickhem, LLC

(57) ABSTRACT

A medical waste fluid collection and disposal system includes a medical waste fluid collection cart including first and second fluid collection canisters. A valve assembly selectively communicates with the canisters and a valve drive system controls the valve assembly. A liquid level sensor is positioned within each of the canisters. A cart processor communicates with the liquid level sensors and the valve drive system. A cart drain line communicates with the valve assembly and a receptacle, a cart flushing line communicates with the valve assembly and the receptacle and a cart data line and a cart power line communicate with the cart processor and the cart receptacle. A station includes a drain pump that communicates with a drainage system and a station drain line, a flushing pump that communicates with a source of washing liquid and a station flushing line and a station processor in communication with the drain and flushing pumps. A station data line communicates with the station processor. A coupler communicates with the station drain line, flushing line and the station data line and a station power line. The station coupler removably engages the cart receptacle so operation of the cart and station components can be coordinated by the processors for drainage and flushing of the cart canisters.

7 Claims, 28 Drawing Sheets

U.S. PATENT DOCUMENTS

| | | |
|---|---|---|
| 5,795,475 A | 8/1998 | Luedke et al. |
| 6,123,093 A | 9/2000 | D'Antonio et al. |
| 6,784,443 B2 | 8/2004 | Pennington et al. ....... 250/506.1 |
| 7,082,969 B1 | 8/2006 | Hollerback |
| 2003/0144422 A1 | 7/2003 | Honeycutt et al. ............ 525/221 |
| 2005/0143685 A1 | 6/2005 | Peyron et al. ................... 604/19 |
| 2007/0028570 A1 | 2/2007 | Dunn et al. |
| 2007/0135779 A1 | 6/2007 | Lalomia et al. ............... 604/319 |
| 2007/0209151 A1 | 9/2007 | Gogel et al. .................... 15/352 |
| 2008/0179344 A1 | 7/2008 | Michaels et al. ................ 222/20 |

OTHER PUBLICATIONS

Collins English Dictionary—Complete and Unabridged© HarperCollins Publishers 1991.

LID ASSEMBLY FOR A MEDICAL WASTE FLUID COLLECTION AND DISPOSAL SYSTEM

CLAIM OF PRIORITY

This application is a division of U.S. patent application Ser. No. 12/245,966, filed Oct. 6, 2008 now U.S. Pat. No. 8,292,857, which claims the benefit of U.S. Provisional Patent Application Ser. No. 60/997,787, filed Oct. 4, 2007.

BACKGROUND

The invention relates generally to systems for handling biological fluids and, in particular, to an automated system for collecting waste fluids during medical procedures and safely disposing of the waste fluids.

DESCRIPTION OF EMBODIMENTS

Figure 1:
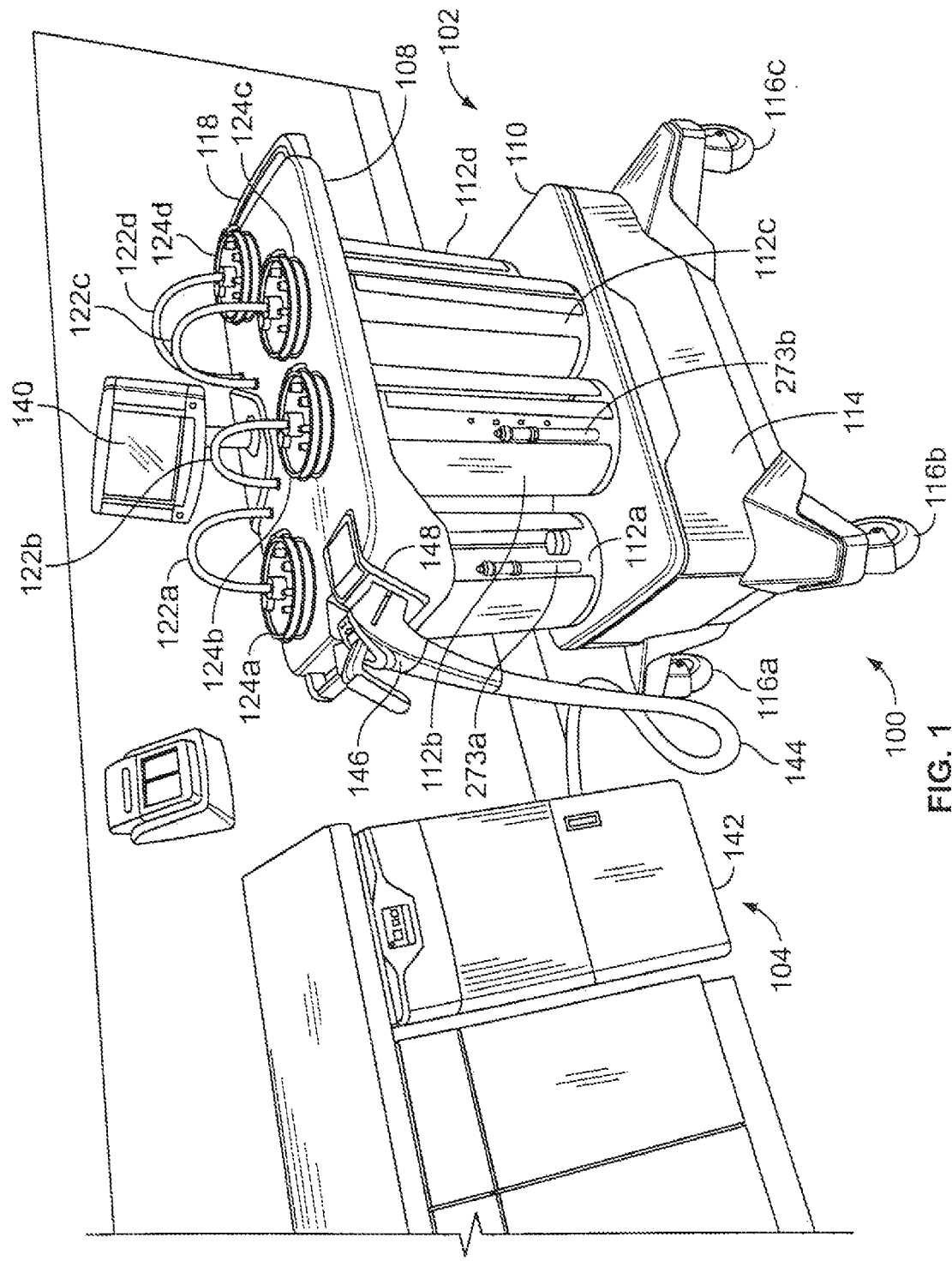
FIG. 1 is a perspective view of an embodiment of the system of the invention, including a first embodiment of the cart.

An embodiment of the system of the present invention, is indicated in general at 100 in FIG. 1. The system includes a cart, indicated in general at 102, and an evacuation station, indicated in general at 104.

The cart features a top plate 108 and a bottom plate 110. Positioned between the top and bottom plates are fluid collection cylinders 112a-112d. While four cylinders are shown in FIG. 1, the cart may feature an alternative number of cylinders, such as two in the case of the alternative embodiment discussed below. The cart also features a bottom cabinet, indicated at 114, that is mounted on casters 116a-116d which offer steering capability for the cart. The casters also preferably include a brake feature. Such casters are well-known in the art. The top plate 108 features a handle 118. As a result, the cart may be easily pushed to and from an operating room.

Figure 2:
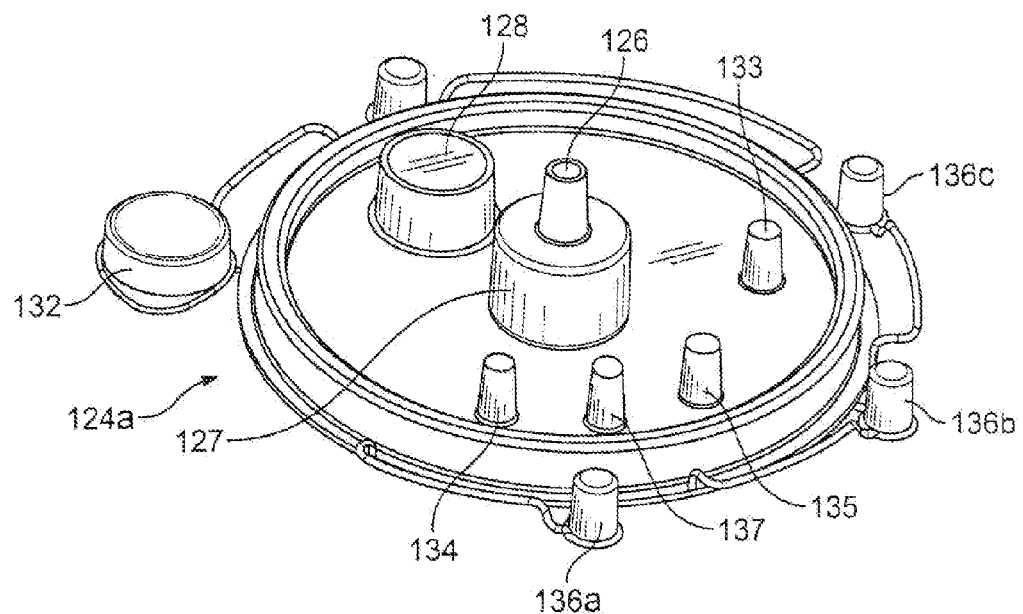
FIG. 2 is an enlarged perspective view of one of the cylinder lids of FIG. 1.

As will be described in greater detail below, each of the cylinders 112a-112d are connected to a vacuum source via flexible tubing 122a-122d and their lids 124a-124d. An enlarged view of one of the lids is provided in FIG. 2, where the lid is indicated in general at 124a. The lid is preferably constructed of molded plastic and is disposable. Flexible tubing 122a of FIG. 1 attaches at one end to vacuum port 126, with the opposite end attaching to a vacuum pump as described below. The vacuum port is provided with a filter, preferably a hydrophobic filter, positioned in compartment 127 (FIG. 2). Normally when in use during a medical procedure, the accessory port 128 is covered by cap 132. A patient out suction tube is connected to the ortho port 133, while a tandem port 134 and an patient port 135 are covered by two of the caps 136a-136d. The lid 124a also includes tubing post 137 for occluded vacuum with the patient tubing. The same applies for the remaining cylinder lids 124b-124d of FIG. 1. As a result, suction is selectively drawn on each cylinder so that fluids may be collected therein during the medical procedure via the suction tubing. The suction and other functions of the cart are controlled via a touch screen 140 of FIG. 1.

After the cart 102 is used in an operating room procedure, and fluids have been collected in one or more of the cylinders 112a-112d, the patient suction tubing is removed from the cylinder lids and all ports for each cylinder lid to which suction was applied are covered with caps (such as one of the caps 136a-136d of FIG. 2 for lid 124a). The cart is then rolled to a positioned adjacent to the evacuation station 104 for draining, washing, disinfecting, rinsing and return to a suction collection state, as illustrated in FIG. 1.

Evacuation station 104 includes a housing 142 that contains a source of disinfection solution, pump, drainage system and other components, which are described below, for draining, washing and disinfecting the cylinders of cart 102. As will be explained in greater detail below, the evacuation station 104 communicates with cart 102 by way of composite hose 144 and coupler 146. As illustrated in FIG. 1, coupler 146 is received within a receptacle 148 of the cart. When the draining, washing and disinfecting of the cart cylinders is complete, the coupler 146 is removed from the cart receptacle 148 so that the cart may again be rolled to an operating room for use.

Enlarged and sectional views of the coupler 136 of the system of FIG. 1 are presented in FIGS. 3-8. Prior art systems, such as the one illustrated in commonly assigned U.S. Pat. No. 7,090,663, require that multiple fluid lines and an electrical line be individually connected between the cart and the evacuation station. The coupler 146 permits a single connection to be made between the cart and station. This simplifies and expedites connecting the cart to, and disconnecting the cart from, the evacuation station.

Figure 3:
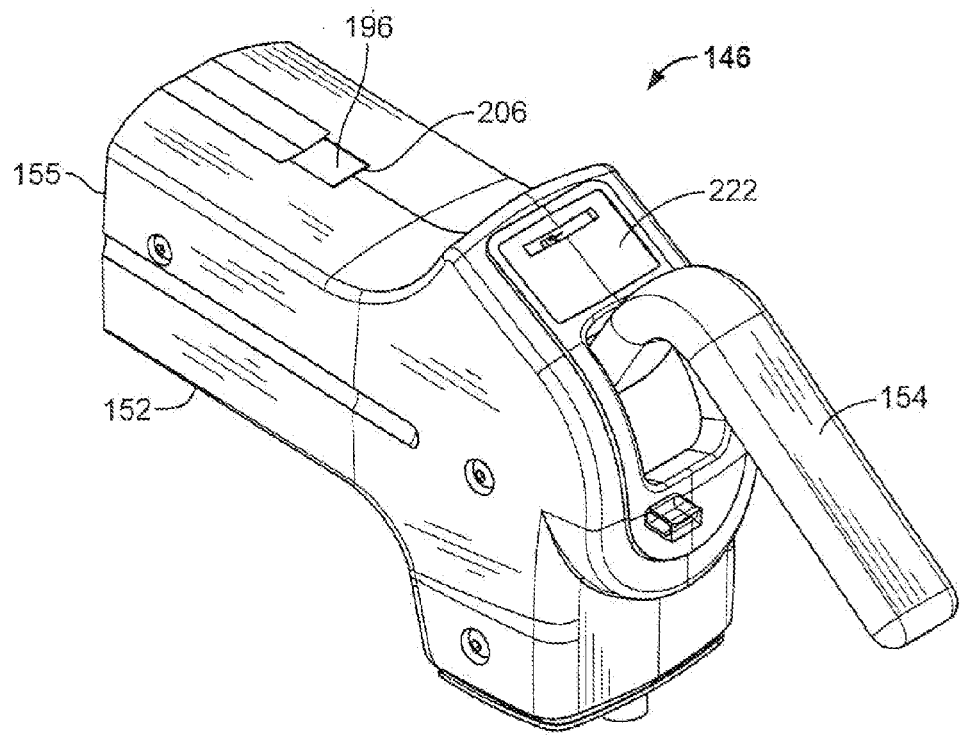
FIG. 3 is an enlarged perspective view of the station coupler of FIG. 1.
Figure 4:
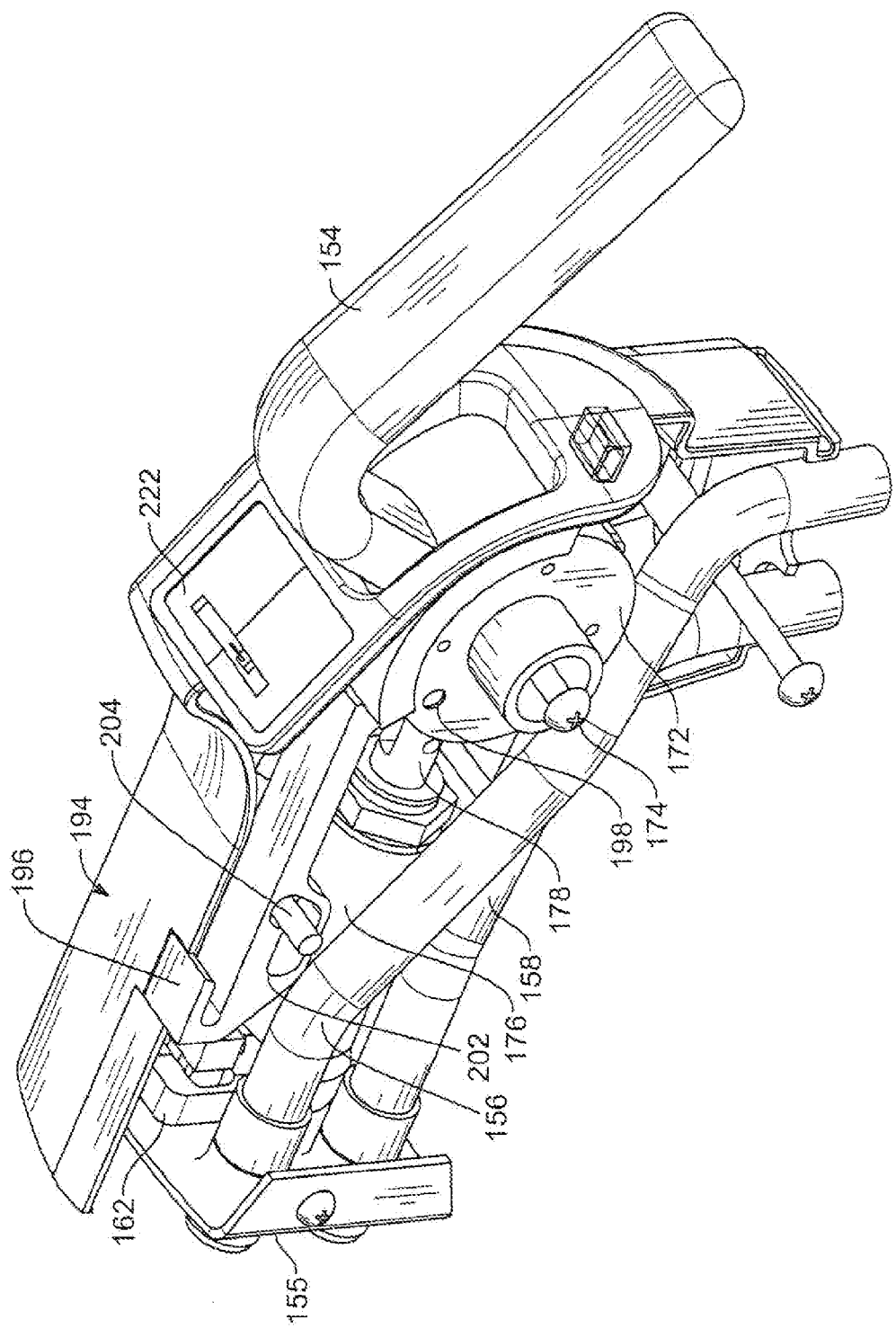
FIG. 4 is a perspective view of the coupler of FIG. 1 with half of the coupler housing removed.
Figure 5:
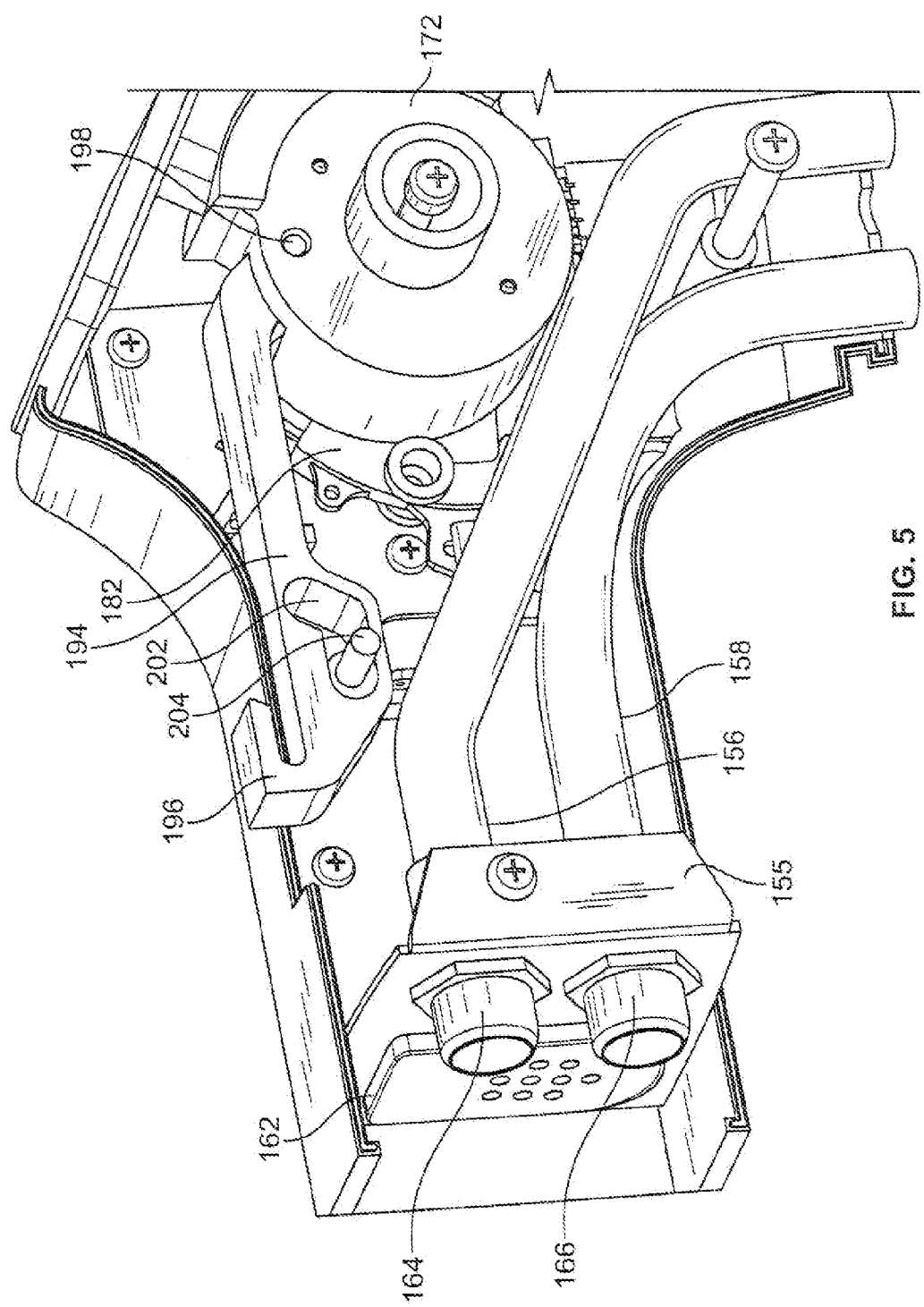
FIG. 5 is an enlarged perspective view of the coupler of FIG. 4.

As illustrated in FIG. 3, the coupler 146 includes a coupler housing 152, a coupler handle 154 and a coupler nose plate 155. FIG. 4 shows the coupler with half of the housing removed. As illustrated in FIG. 4, the coupler features a wash supply line 156 and wash drain line 158. The coupler also features an electrical connector 162, which is position in nose plate 155. As will be explained in greater detail below, the electrical connector provides 24V DC power to the cart for powering a cart processor and operation of the valve drive system, sensors, solenoids and touch screen. The connector also permits data transfer between the cart and the evacuation station processors and provides the cart's safety ground plain connection. As illustrated in FIGS. 4 and 5, the wash supply and drain lines terminate at one end in wash supply and drain fittings 164 and 166, respectively, both of which are positioned on nose plate 155. Wash supply and drain lines 156 and 158, along with an electrical line featuring one end that terminates in electrical connector 162, are combined in a parallel fashion and housed in composite hose 144 of FIG. 1, which is attached to the evacuation station 104, as will be explained below.

Figure 6:
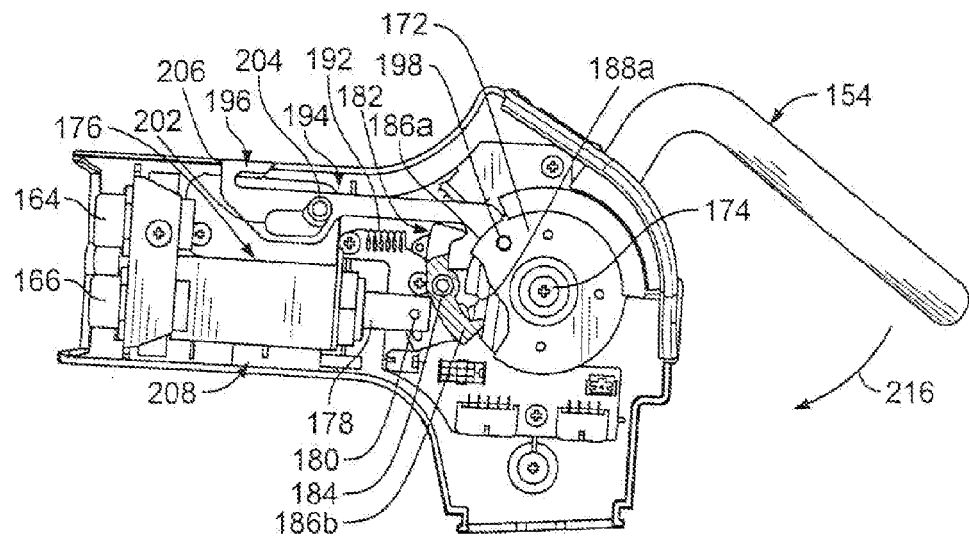
FIG. 6 is a side elevational view of the coupler of FIGS. 3-5 with the handle in a released position.
Figure 7:
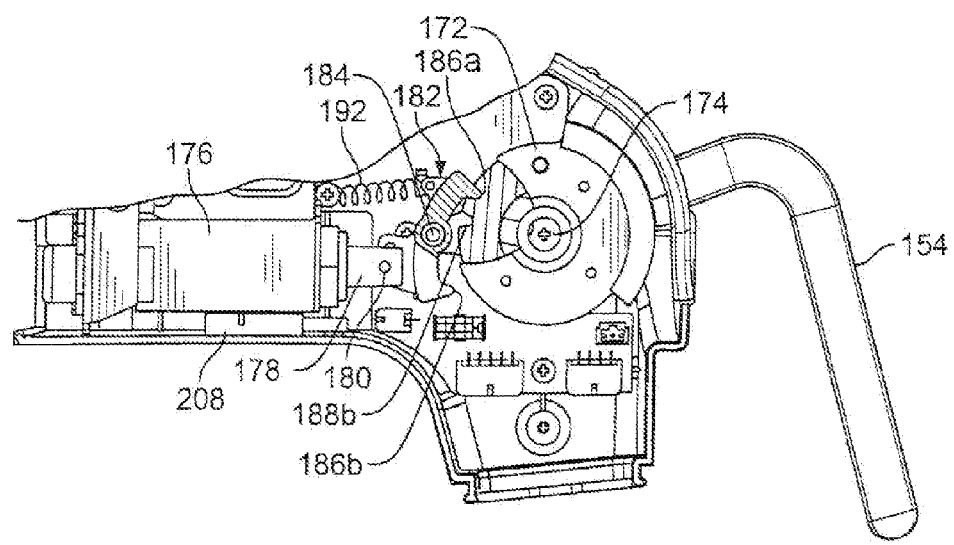
FIG. 7 is a partial side elevational view of the coupler of FIGS. 3-6 with the handle in a locked position.

As illustrated in FIGS. 4-8, the coupler also includes a ratchet wheel 172 to which handle 154 is attached. Ratchet wheel 172 pivots about an axis defined by screw 174. In addition, as illustrated in FIGS. 6 and 7, the coupler includes a solenoid 176 featuring a ram 178 that is attached in a pivoting fashion by pin 180 to a toggle 182. Toggle 182 pivots about pin 184 and features a top tooth 186a and a bottom tooth 186b. Ratchet wheel 172 includes a top notch 188a (FIG. 6) and a bottom notch 188b (FIG. 7). The top portion of toggle 182 is connected to tension coil spring 192 that urges the toggle to pivot about pin 184 in a counter-clockwise direction.

As illustrated in FIGS. 4 and 6 the coupler also features a hook arm, indicated in general at 194. The hook arm features a hook portion 196 at one end and is pivotally connected at the opposing end via pin 198 to ratchet wheel 172. The hook arm also includes a generally L-shaped slot 202 (see also FIGS. 5 and 8) within which pin 204 is received.

When a user initially inserts the coupler in the receptacle of the cart (indicated at 148 in FIG. 1), the coupler is in the configuration illustrated in FIG. 6 (and FIGS. 3 and 4). More specifically, the solenoid 176 is not powered and ram 178, is extended. As a result, the bottom tooth 186b of the toggle is positioned within the bottom slot 188b of the, ratchet wheel 172 and handle 154 is locked in the position illustrated. In addition, the hook portion 196 of the hook arm 194 is recessed within the generally square opening 206 of the coupler housing (as illustrated in FIGS. 3, 4 and 6) so that it is flush with the top surface of the coupler housing.

Figure 8:
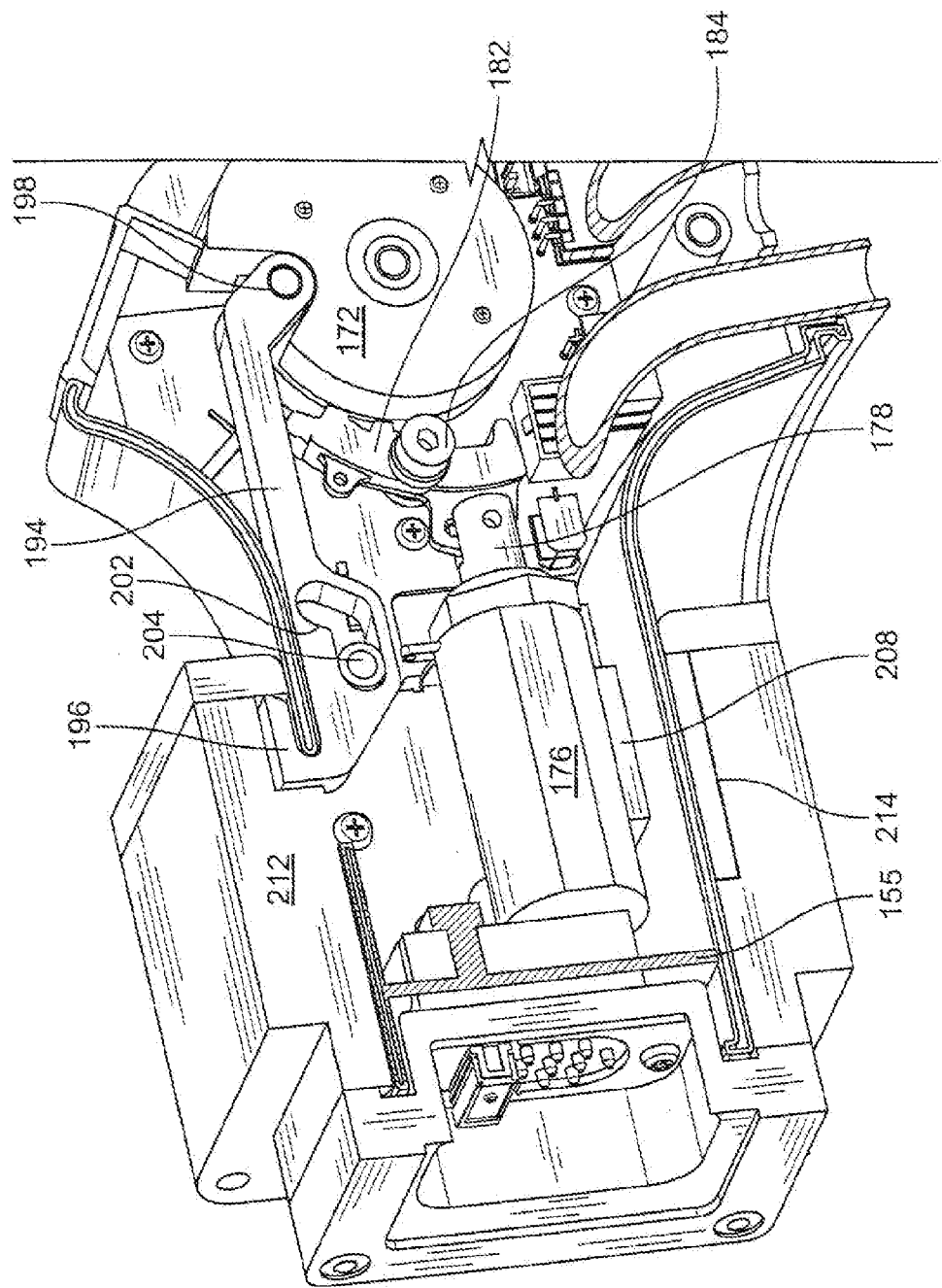
FIG. 8 is a perspective view of the coupler of FIG. 5 in engagement with the socket of the cart receptacle.

As illustrated in FIG. 6-8, the coupler also features a proximity sensor 208, which is positioned adjacent to the interior surface of the bottom of the coupler housing and detects when metal is near. The proximity sensor includes a circuit for determining proximity to metal. As illustrated in FIG. 8, the socket 212 of the cart receptacle (148 in FIG. 1) features a metal strip 214. After the coupler 146 is inserted into the cart receptacle 148, as illustrated in FIGS. 1 and 8, the proximity sensor 208 of the coupler detects the presence of the now adjacent metal strip 214 within the socket of the cart receptacle. The proximity sensor then sends a signal to a switch within the coupler that energizes the solenoid 176 with power received from the evacuation station via electrical connector 162 (FIGS. 4 and 5).

When the solenoid 176 is powered, ram 178 is retracted, as illustrated in FIGS. 7 and 8. As a result, toggle 182 is pivoted about pin 184 in a clockwise direction so that the bottom tooth 186b of the toggle 182 is removed from the lower notch 188b of ratchet wheel 172. As a result, ratchet wheel 172 is free to pivot and the user may rotate the handle 154 in the direction of arrow 216 of FIG. 6 from a release position (illustrated in FIG. 6) into the lock position shown in FIG. 7. As this occurs, the ratchet wheel 172 rotates in a clockwise direction about screw and pivot axis 174 until the upper tooth 186a of the toggle engages the upper notch 188a of the ratchet wheel 172.

As the ratchet wheel 172 rotates clockwise, while the user is rotating handle 154, the hook arm is pulled to the right of FIG. 6 by pin 198. As a result, pin 204 travels through the generally L-shaped slot 206 from the position illustrated in FIG. 6 to the position illustrated in FIGS. 5 and 8. This causes the hook portion 196 of the hook arm to rise up through opening 206 (FIGS. 3 and 6) of the top surface of the coupler housing to the position illustrated in FIGS. 5 and 8. As a result, with reference to FIG. 8, the hook portion 196 engages a corresponding notch 220 formed in the socket 212 of the cart receptacle (148 in FIG. 1) so that the coupler cannot be withdrawn from the cart receptacle. In addition, when the hook portion 196 engages the socket 212, it aids in engagement by pulling coupler into the receptacle as the handle is rotated downwards. This provides a mechanical advantage for the insertion of the wash supply and drain fittings 164 and 166 into the corresponding ports, and O-rings, of the socket.

Due to the engagement of the upper tooth 186a of the toggle with the upper notch 188a of the ratchet wheel, as illustrated in FIGS. 4, 7 and 8, the handle 154 of the coupler is locked in the position illustrated in FIG. 7 until the solenoid 176 is de-energized and the ram 178 returns to the original extended position illustrated in FIG. 6 (as the coil spring 192 contracts). The coupler is therefore locked within the socket of the cart receptacle, as illustrated in FIGS. 1 and 8, until the solenoid 176 (FIGS. 6-8) is de-energized. As illustrated in FIGS. 3 and 4, the coupler features an "emergency release" button 222 that de-energizes the solenoid 176 so that the handle 154 may be lifted into the position illustrated in FIGS. 3, 4 and 6, and the coupler removed from the cart receptacle.

Figure 9:
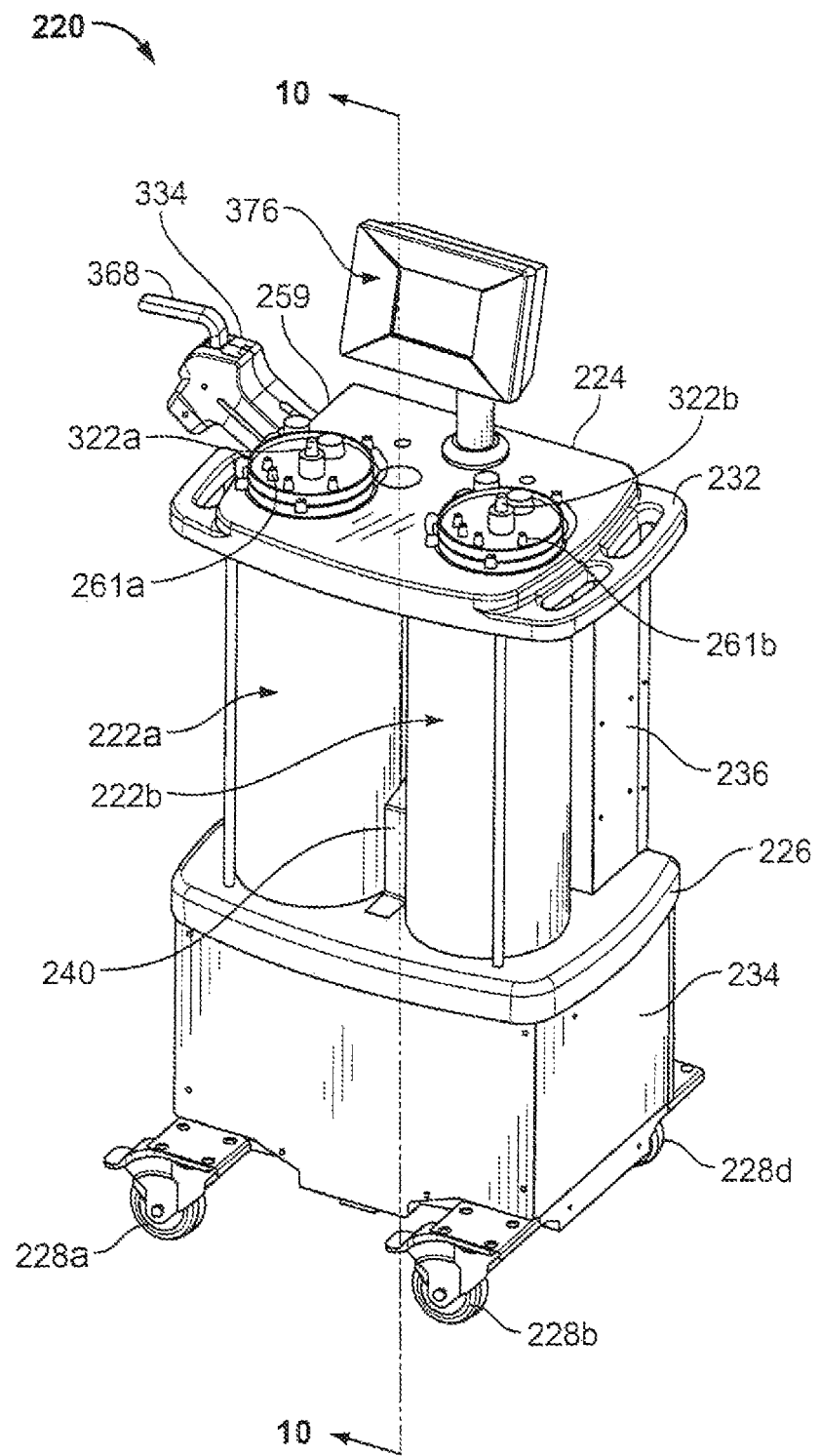
FIG. 9 is a front perspective view of a second embodiment of the cart of the system of the invention.
Figure 10:
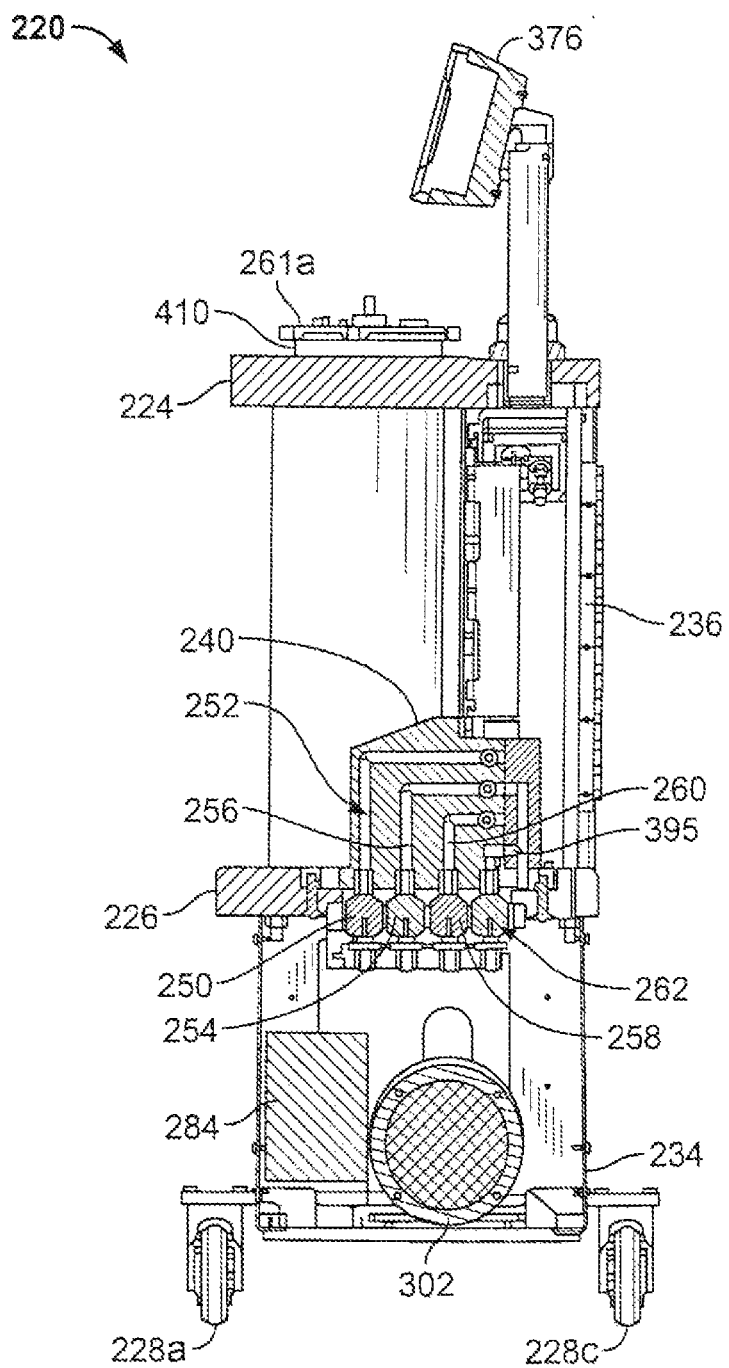
FIG. 10 is a sectional view of the cart taken along line 10-10 Of FIG. 9.

An embodiment of the cart of the system featuring two fluid collection canisters is indicated in general at 220 in FIGS. 9 and 10. As described previously with reference to the embodiment of the cart of FIG. 1, in this embodiment, the canisters are two cylinders, indicated at 222a and 222b in FIGS. 9 and 10, are positioned between a top plate 224 and a bottom plate 226. Circular portions of the bottom plate 226 form the bottoms of the cylinders 222a and 222b. The cylinders are preferably constructed of acrylic and may feature a fluorinated coating for easier cleaning. The cylinders may also be constructed from a variety of alternative materials including, but not limited to, glass and plastic. The cart is mounted on casters 228a-228d and top plate 224 features a handle 232 so that the cart may be easily pushed to and from an operating room.

Figure 11:
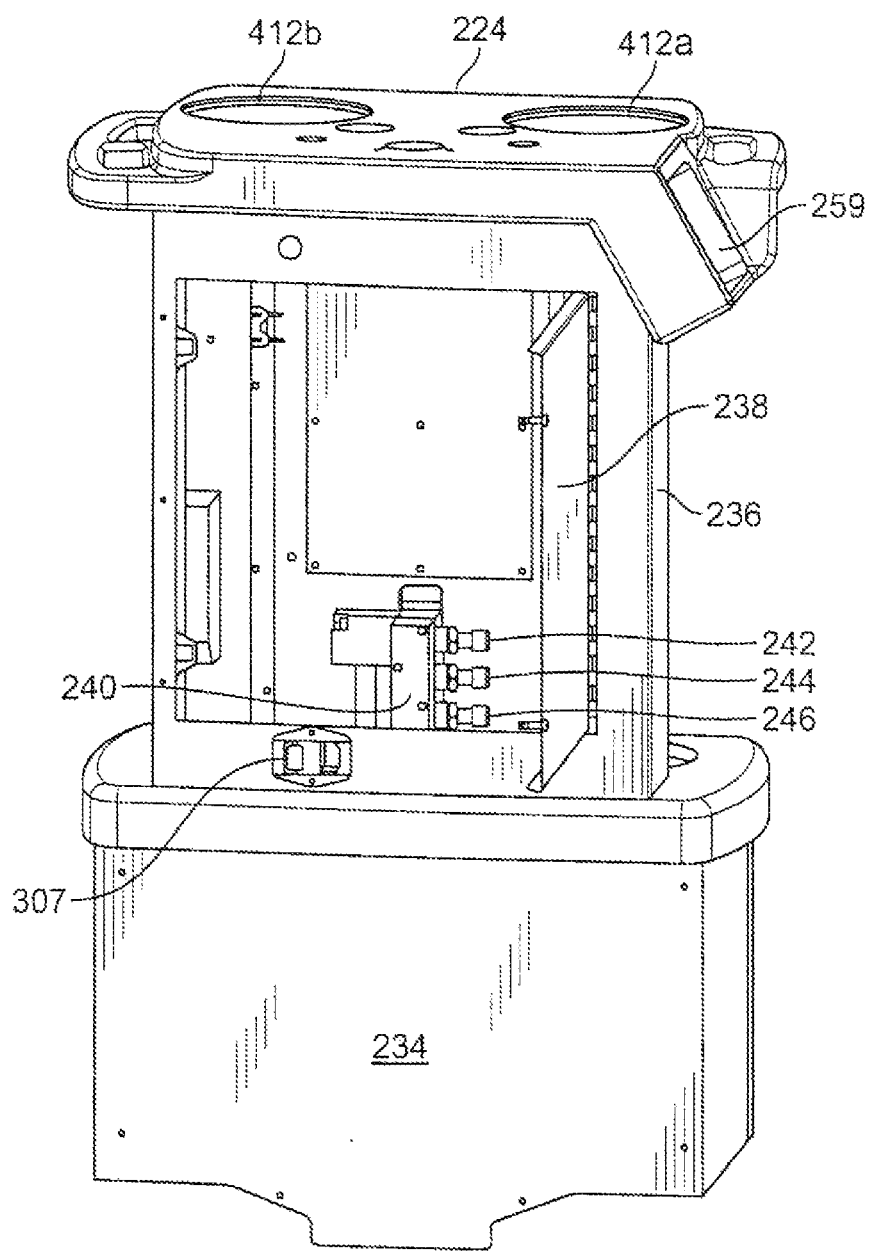
FIG. 11 is a partial rear perspective view of the cart of FIGS. 9 and 10.

As illustrated in FIGS. 9-11, the cart also features a bottom cabinet, indicated at 234, as well as a back cabinet, indicated at 236. As illustrated in FIG. 11, the back cabinet 236 features a door 238 that permits access to its interior.

As illustrated in FIGS. 9-11, a fluid manifold 240 is positioned between cylinders 222a and 222b and extends into the interior of back cabinet 236. As illustrated in FIG. 11, the fluid manifold includes a "wash" tube fitting 242, a "drain" tube fitting 244 and a "vent" tube fitting 246. The "wash" tube fitting (242 in FIG. 11) communicates with a 3-Way "wash" valve, illustrated at 250 in FIG. 10, via fluid passage 252, also illustrated in FIG. 10. The "drain" tube fitting (244 in FIG. 11) similarly communicates with a 3-way "drain" valve, illustrated at 254 in FIG. 10, via fluid passage 256, also illustrated in FIG. 10. The "vent" tube fitting (246 in FIG. 11) similarly communicates with a 3-way "vent" valve, illustrated at 258 in FIG. 10, via fluid passage 260, also illustrated in FIG. 10.

As will be explained in greater detail below, wash tube fitting 242 communicates with the cart receptacle 259 (FIG. 11) via flexible tubing (not shown) so that it may receive water and cleaning and disinfecting solution from, with reference to FIG. 1, the composite hose 144 and coupler 146 of the evacuation station 104. The drain tube fitting 244 similarly communicates with the cart receptacle (259 in FIG. 11) via flexible tubing (not shown) so that it may direct waste fluid to the evacuation station via the coupler and composite hose of the station. Vent tube fitting 246 communicates with the interiors of the cylinders via flexible tubing (not shown) and vent ports formed in the cylinder lids (illustrated at 261a and 261b in FIG. 9).

Figure 12:
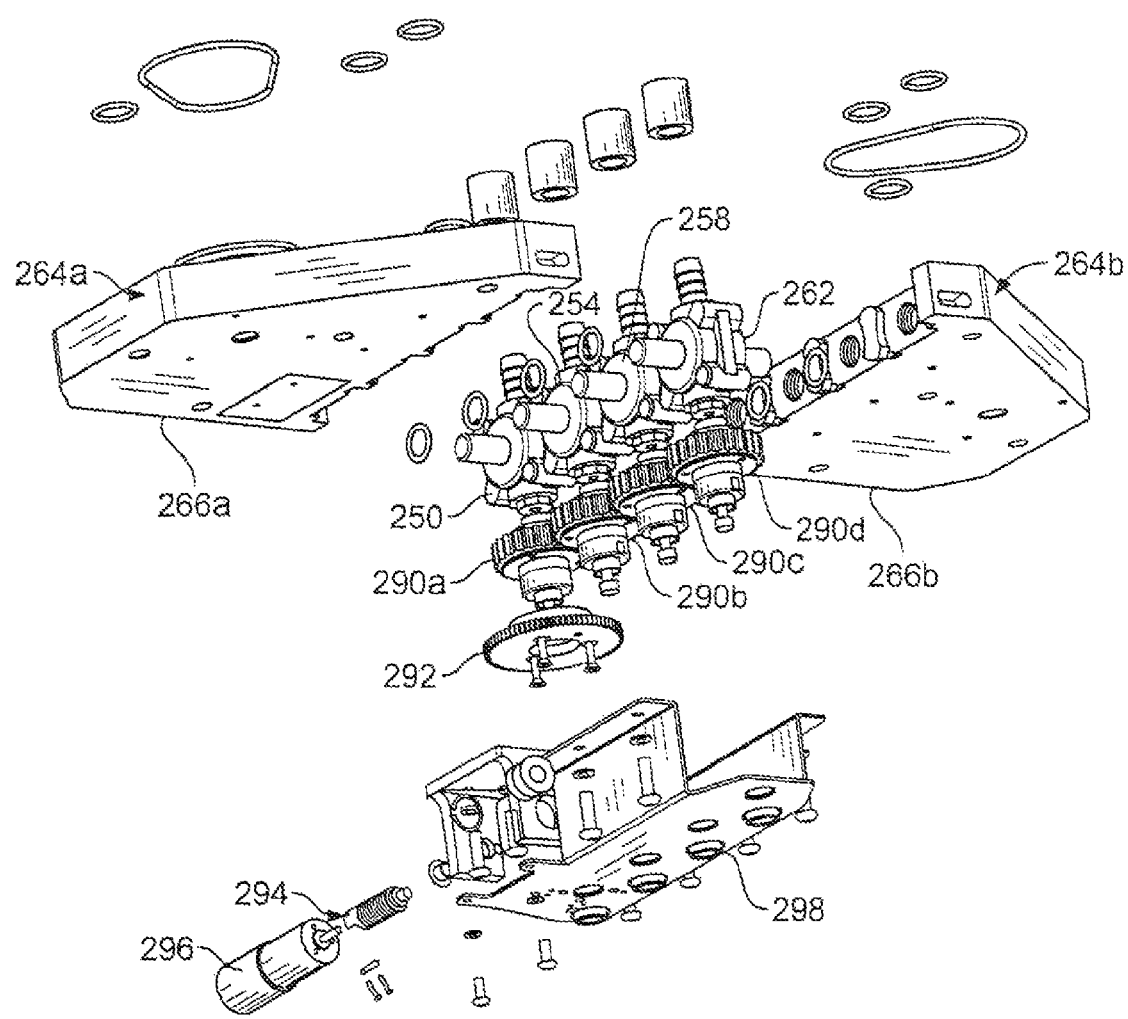
FIG. 12 is an exploded enlarged perspective view of the valve assembly and valve drive system of the cart of FIGS. 9-12.

As illustrated in FIG. 12, valve 250, drain valve 254, vent valve 238 and a short loop valve 262 (also shown in FIG. 10) are positioned between left and right manifold blocks 264a and 264b. The manifold blocks 264a and 264b feature leading ends 266a and 266b, respectively, which face the front of the cart.

Figure 13:
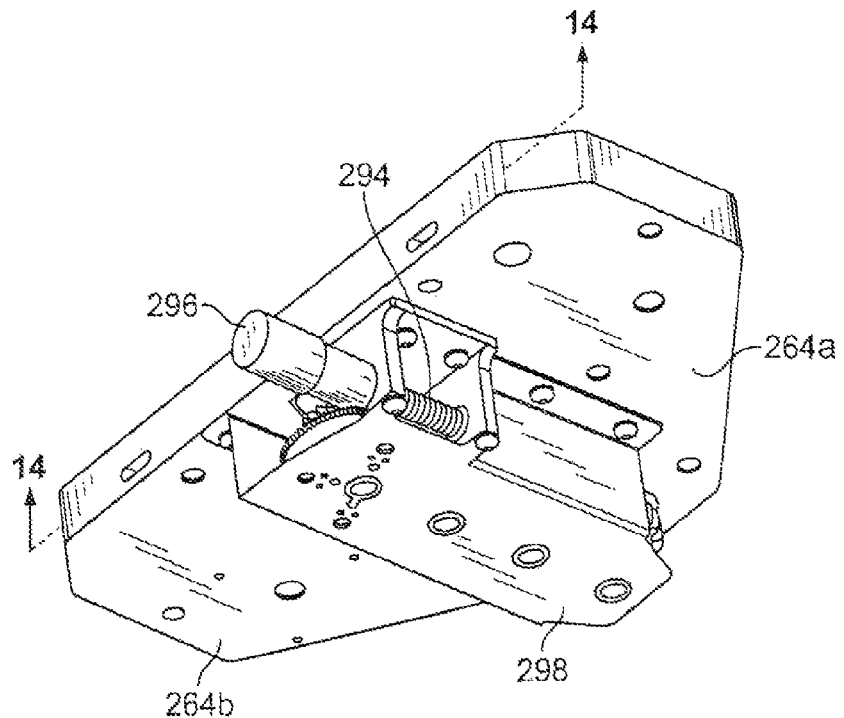
FIG. 13 is a bottom perspective view of the valve assembly and valve drive system of FIG. 12 after assembly.
Figure 14:
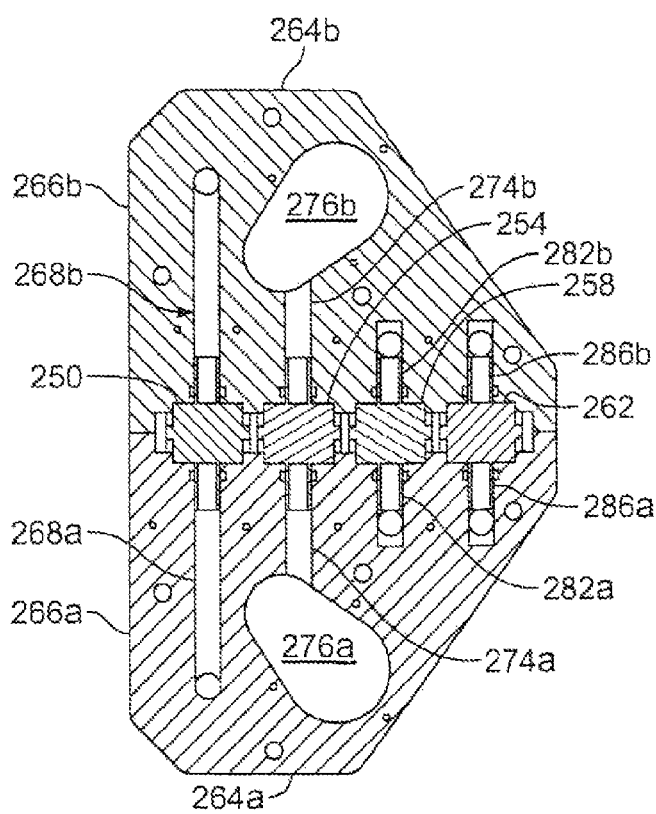
FIG. 14 is a sectional view of the valve assembly taken along line 14-14 of FIG. 13.

As illustrated in FIG. 14, which is a sectional view taken from the assembled manifold blocks illustrated in FIG. 13, the wash valve 250 communicates with fluid passages 268a and 268b. The fluid passages 268a and 268b lead to and communicate with cleaning nozzles, which connect to base ports 272a and 272b in FIG. 15. The nozzles, examples of which are illustrated at 273a and 273b in FIG. 1, rotate when water, cleaning and disinfecting solutions are supplied thereto in the manner described below. As a result, the nozzles spray the interior of the cylinders (222a and 222b of FIGS. 9 and 10) so that they are cleaned, disinfected and drained.

Figure 15:
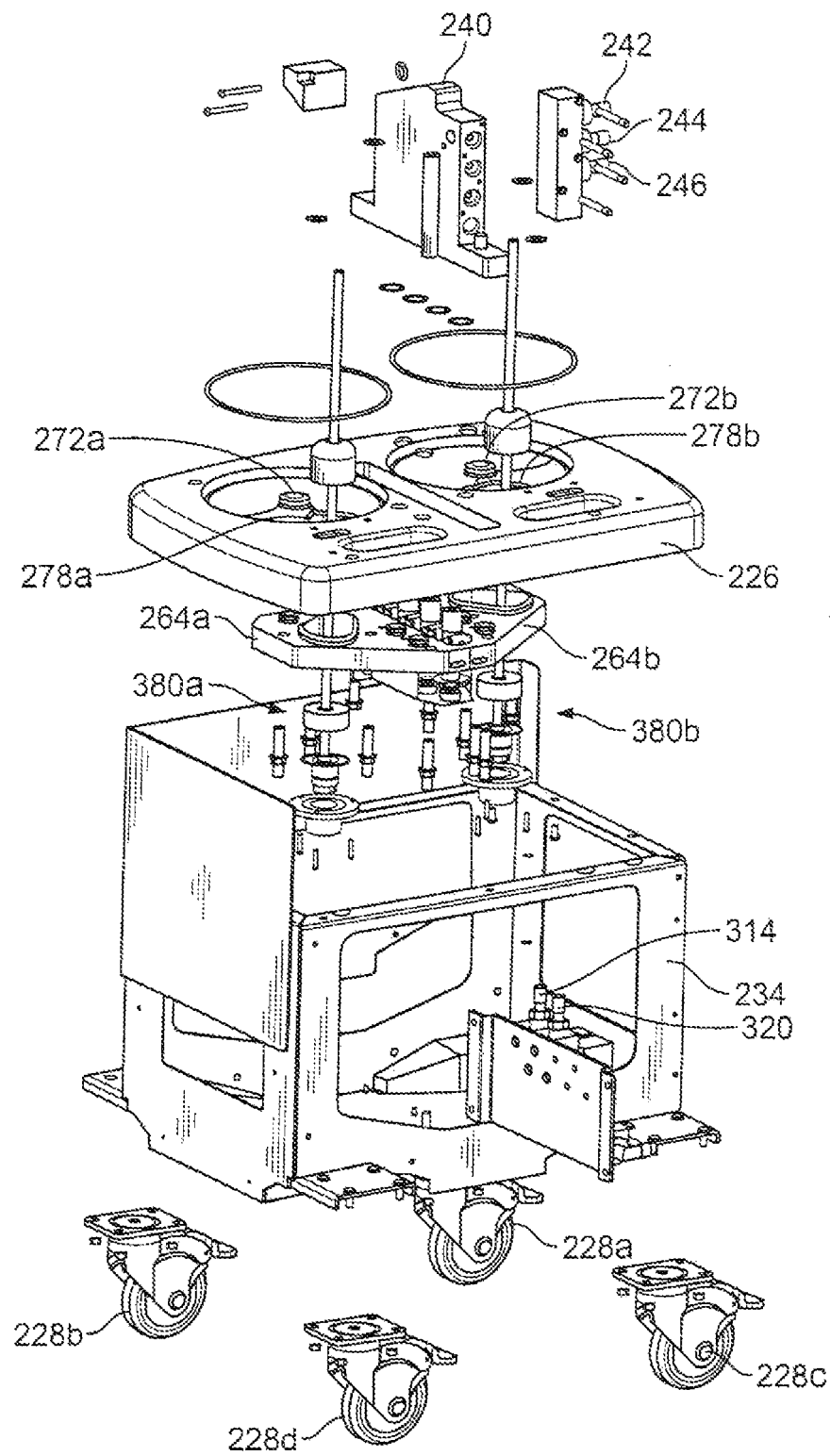
FIG. 15 is an enlarged exploded view of the lower portion of the cart of FIGS. 9-11.

In addition, FIG. 14 illustrates that the drain valve 254 communicates with fluid passages 274a and 274b, which terminate into oblong recesses 276a and 276b which, as illustrated in FIG. 15 communicate with correspondingly sized and shaped openings 278a and 278b formed in bottom plate 226. As a result, the drain valve 254 communicates with the interior of each cylinder (222a and 222b in FIG. 9).

Vent valve 258, as illustrated in FIG. 14 communicates with fluid passages 282a and 282b. As will be explained in greater detail below, the fluid passages communicate with a gas collector, illustrated at 284 in FIGS. 10 (and 16), via flexible tubing. Gas collector 284, may be periodically connected to the hospital building ventilation system for venting to the exterior of the building.

Short loop valve 262, as illustrated in FIG. 14, communicates with fluid passages 286a and 286b. As will be explained in greater detail below, the fluid passages selectively communicate with the supply of water and cleaning and disinfecting solutions from the system station to avoid drips when the station coupler (146 in FIG. 1) is disconnected from the cart.

Returning to FIG. 12, valves 250, 254, 258 and 262 are controlled via a valve drive system that includes a gear train featuring gears 290a, 290b, 290c and 290d. A main drive gear 292 is connected to gear 290a so that they turn in unison. The main drive gear is engaged by a worm gear 294 which is selectively rotated by an electric drive motor 296. As a result, the configuration of the valves 250, 254, 258 and 262 may be controlled by activation of the electric drive motor 296. As illustrated in FIGS. 12 and 13, the gear train, main drive gear, worm gear and electric drive motor are secured to the manifold blocks 264a and 264b by drive housing 298.

As mentioned previously, valves 250, 254, 258 and 262 are 3-way valves. The configurations of valves 250, 254 and 258 include simultaneously "on" for cylinder 222a only, simultaneously "on" for cylinder 222b only or simultaneously "off" for both cylinders. When the valves are configured to be "on" for cylinder 222a only, water and cleaning and disinfecting solution are provided to cylinder 222a and drainage and venting are provided for cylinder 222a. When the valves are configured to be "on" for cylinder 222b only, water and cleaning and disinfecting solution are provided to cylinder 222b and drainage and venting are provided for cylinder 222b. When valves 250, 254 and 258 are configured in either one of the two "on" positions, short loop valve 262 is configured in an "off" position. When valves 250, 254 and 258 are each configured in the "off" position, short loop valve 262 is configured in an"on" position, the impact of which will be described below.

Additional details and operation of the system will now be described with regard to FIGS. 16 and 17, which show schematics of the cart and station, respectively, as well as FIG. 18, which illustrates the configurations of the cart valves during evacuation of the cylinders and use in the operating room.

Figure 16:
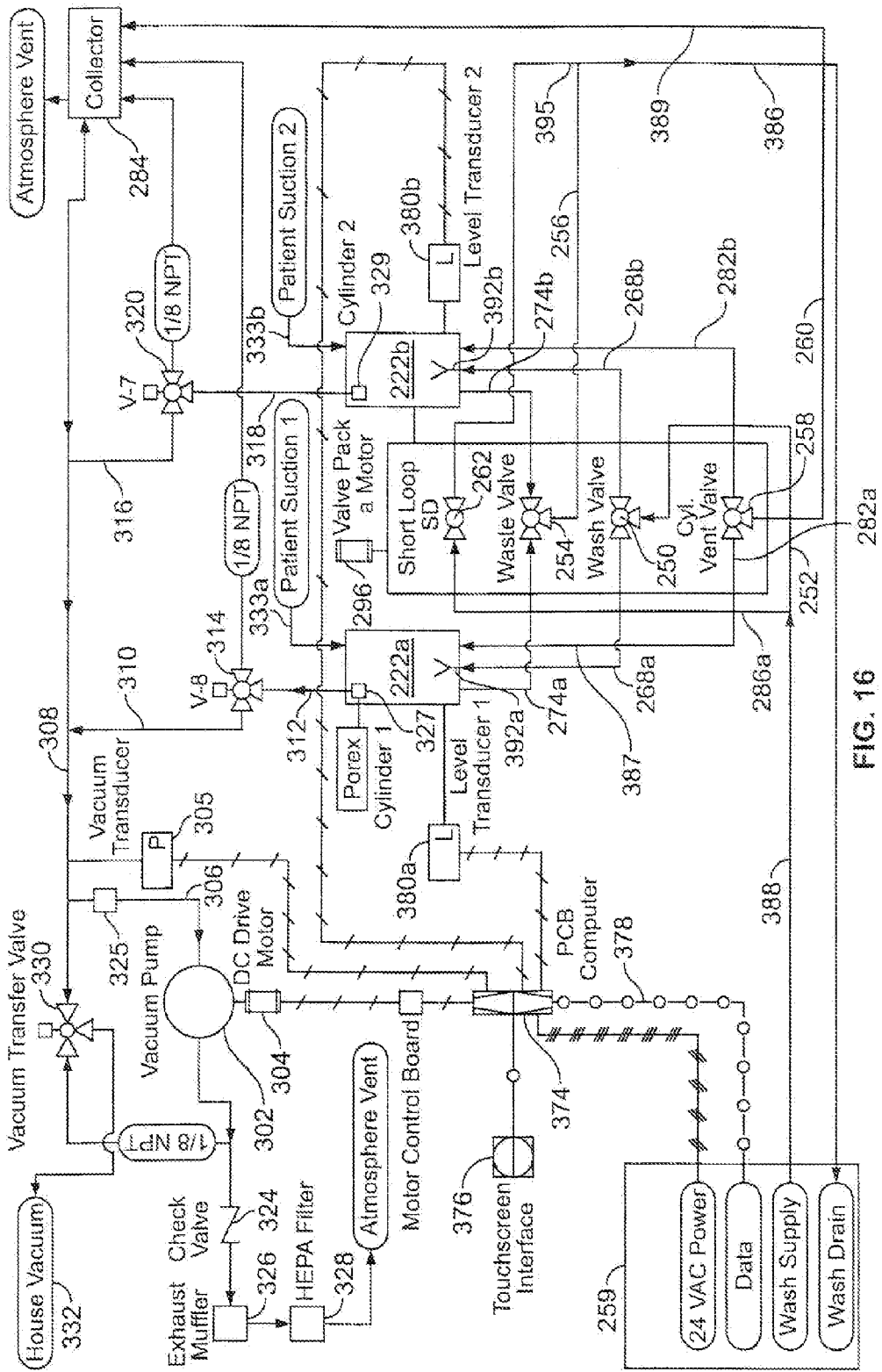
FIG. 16 is schematic of the cart of FIGS. 9-15.

A schematic of the cart of FIGS. 9-15, is illustrated in FIG. 16. As illustrated in FIG. 16, the cart features a vacuum pump 302 that is driven by an electric drive motor 304. When in the operating room, the electric drive motor 304 of the pump receives power via 120V power hookup 307 of FIG. 11. The vacuum pump 302 is also illustrated in FIG. 10 and can feature a variable speed motor (304 in FIG. 16) so that a variety of suction levels may be provided by the cart. As an alternative to a variable speed pump, individual regulating lines may be used to provide variable suction levels. The suction provided by the pump 302 is detected by pressure sensor 305 which, as will be explained below, communicates with the cart processor. As illustrated in FIG. 16, the vacuum pump 302 selectively communicates with cylinder 222a via lines 306, 308, 310 and 312 and valve 314 and/or cylinder 222b via lines 306, 308, 316 and 318 and valve 320. Valves 314 and 320 are also illustrated in FIG. 15 and are positioned within the bottom cabinet 234 of the cart. Lines 312 and 318 of FIG. 16 are actually flexible tubing that connect the vacuum ports of the cylinder lids, illustrated at 322a and 322b in FIG. 9, with valves 314 and 320.

Suction may therefore be pulled on either cylinder 222a or 222b individually, or suction may be pulled on both cylinders simultaneously, by vacuum pump 302. Exhaust air exiting the vacuum pump 302 travels through check valve 324, exhaust muffler 326 and particulate filter 328 before venting to the operating room/atmosphere or hospital suction system. Filtration is provided for the pump input via HEPA bio-filter 325 of FIG. 16. As a result, as explained above with regard to FIGS. 1 and 2, patient suction lines, illustrated at 333a and 333b in FIG. 16, may be connected to patient ports in the cylinder lids (261a and 261b in FIG. 9) so that waste fluids may be collected in either or both cylinders 222a and 222b during a surgical procedure.

The cart protects the filter 328 and the HEPA bio-filter 325 by use of a hydrophobic pre-filters in the canister lids, illustrated at 327 and 329 in FIG. 16, and a sensor to detect if filter 328 becomes wet or damaged so that it would be ineffective. This may be done by a sensor that detects pressure differential change in the air flow across the filter.

As illustrated in FIG. 16, the cart also features a vacuum transfer valve 330 allowing a hospital vacuum system 332 to be used when ultra-low vacuum is required for suction.

When the cart is wheeled out of the operating room, either or both cylinders 222a and 222b will be at lease partially filled with waste fluid from the surgical procedure. To drain, wash and disinfect the cylinder(s), the cart must be positioned adjacent to the system evacuation station and the station coupler positioned within the cart receptacle, as illustrated for cart 102 and evacuation station 104 of FIG. 1.

Figure 17A:
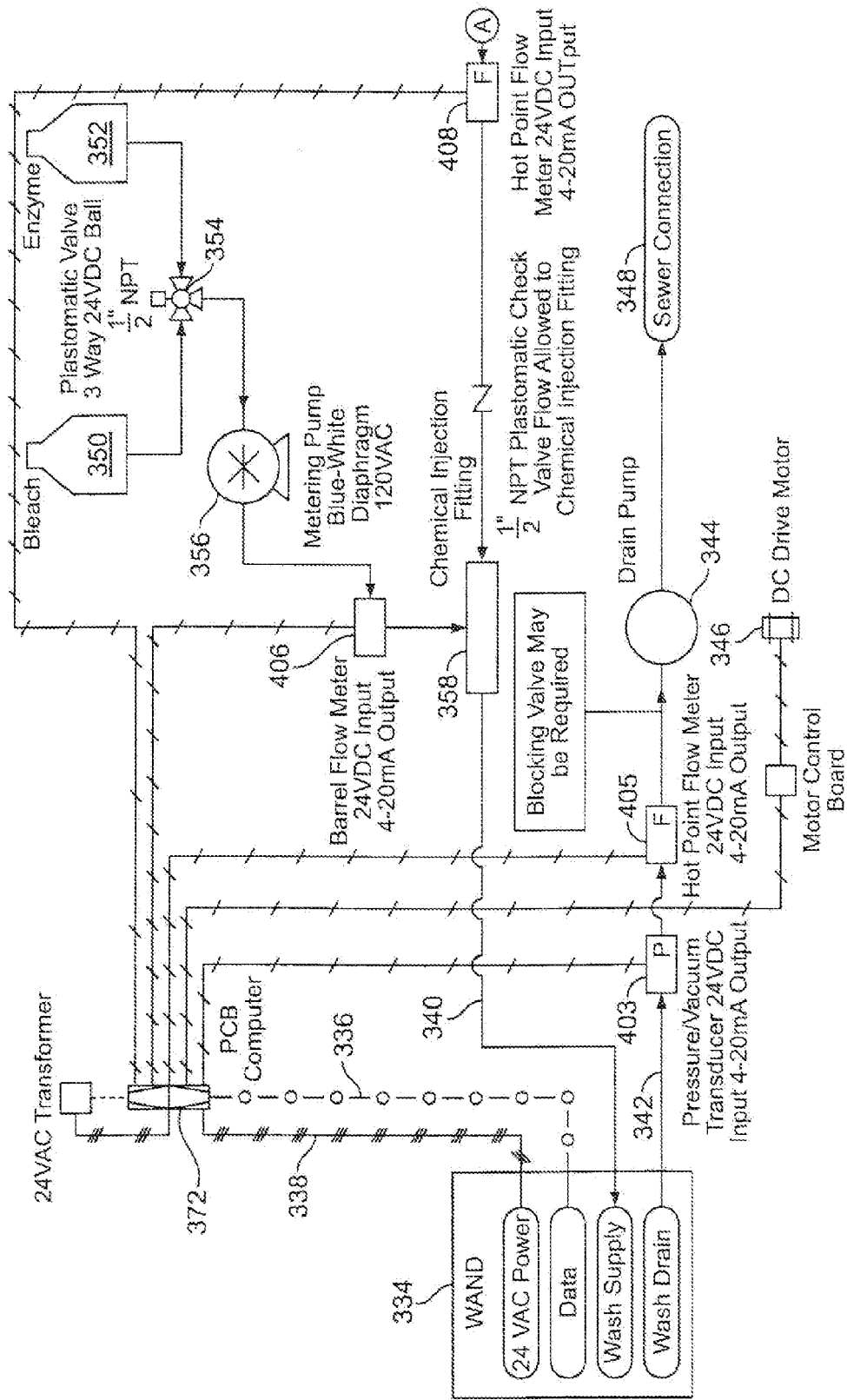
FIG. 17 is a schematic of an embodiment of the station of the invention.
Figure 17B:
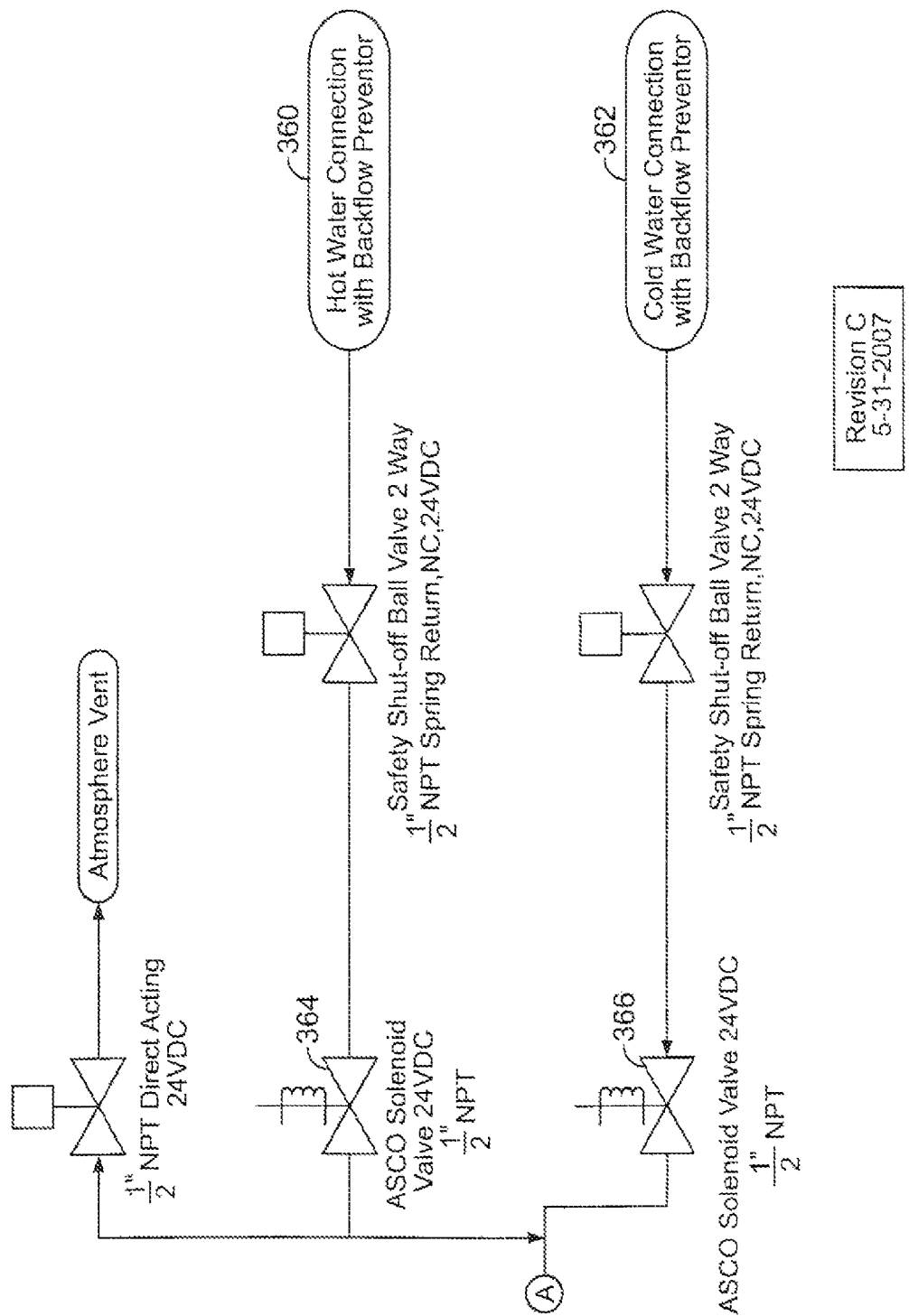

A schematic of an embodiment of the evacuation station is provided in FIG. 17. As illustrated in FIG. 17, the station includes a coupler 334 (also illustrated in FIG. 9) which is coupled to the station by a composite hose (such as illustrated by composite hose 144 of FIG. 1) that includes data link 336, power lines 338, wash supply line 340 and drain line 342, along with corresponding connectors in the coupler 334. The wash drain line 342 communicates with a drain pump 344, which is powered by electric drive motor 346. The outlet of the drain pump communicates with the hospital sewer connection 348. The wash supply line 340 communicates with a supply of bleach 350 and a supply of enzyme 352 via a valve 354, a flushing pump 356 and a chemical injection fitting 358. The chemical injection fitting 358 also receives water from hot water connection 360 and cold water connection 362 through solenoid valves 364 and 366.

When the coupler 334 (FIG. 17) of the station is inserted into the receptacle 259 (FIG. 16) of the cart, as illustrated in FIG. 9, the power, data, wash supply and drain connectors in the coupler and receptacle engage. Next, the handle of the coupler 368 (FIG. 9) is pivoted down, as described with reference to FIGS. 3-8 above. Indeed, the coupler 334 of FIGS. 9 and 17 features the same construction as the coupler 146 of FIGS. 3-8 and operates in the same fashion.

As illustrated in FIG. 17, the station features a processor 372, while the cart, as illustrated in FIG. 16, features a processor 374. The processor 374 of the cart communicates with a touch screen 376 (also shown in FIGS. 9 and 10), which controls operation of the system both when the cart is connected to the evacuation station, and when the cart is being used in the operating room. When the cart is being used in the operating room, the cart processor and touch screen receive power through the 120V AC hookup 307 of FIG. 11, after it is converted to 24V DC with a power supply on board the cart. With regard to the latter, the cart computer 374, based on user inputs through the touch screen 376, controls operation of valves 314 and 320 of FIG. 16 as well as the speed of vacuum pump drive motor 304 and the configuration of vacuum transfer valve 330 to control the level of vacuum provided for each cylinder.

With the cart and station connected through coupler 334 and receptacle 259, cart data line 378 (FIG. 16) and station data line 336 (FIG. 17) permit the cart and station processors to communicate so that the user can control both, and therefore the draining, washing and disinfecting operations, via the touch screen 376.

When the cart and station are connected, the cart processor determines whether or not there is waste fluid in either cylinder 222a or 222b or both. This is accomplished via level transducers 380a and 380b. The transducers preferably take the form of the magnorestrictive liquid level sensors, indicated in general at 380a and 380b in FIG. 15.

Figure 18C:
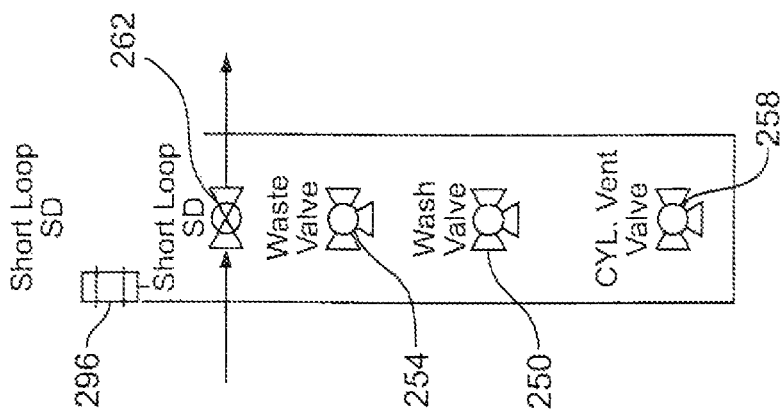
FIGS. 18A-18C are schematics illustrating configurations of the cart valves of FIG. 16.

When the cart is being used in surgery to provide suction to a patient, wash valve 250, waste valve 254 and vent valve 258 are closed, while short loop valve 262 is open. This valve configuration is illustrated in FIG. 18C. When the cart processor 374 detects, via the canister liquid level transducers, that either canister 222a and 222b is nearly filled with liquid waste, an audible/audio and/or optical/visual warning is provided to allow operator to change to the other cylinder. The optical warning may include an illuminated "X" over graphic displays of the canisters on the touch screen 376. The audible warning may include activation of a buzzer, bell or any other audio device which may be positioned in the touch screen housing or otherwise on the cart.

Figure 18B:
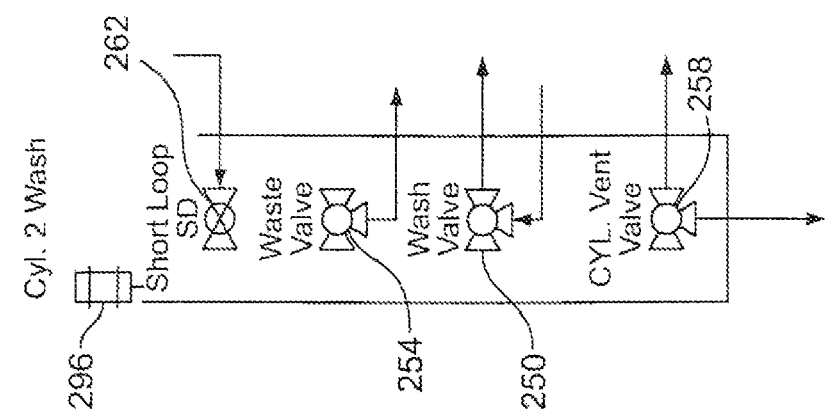
Figure 18A:
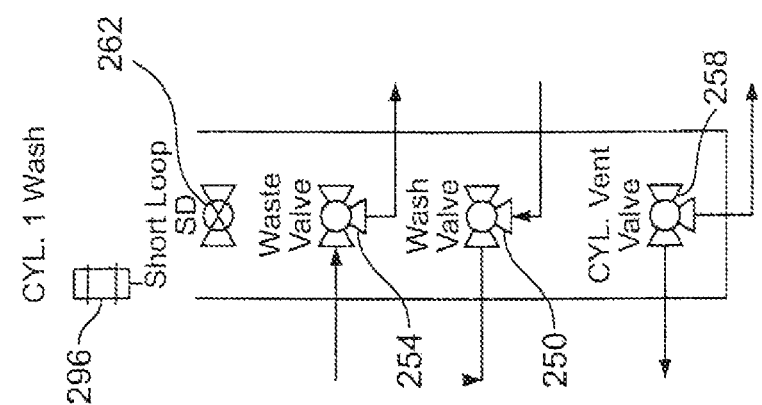

When the cart is connected to the station, if the cart processor determines that there is liquid waste in cylinder 222a, or liquid waste in both cylinders 222a and 222b, the cart processor energizes electric valve drive motor 296 so that the wash, drain, vent and short loop valves 250, 254, 258 and 262, respectively, are placed in the configuration illustrated in FIG. 18A. The cart processor then communicates to the station processor that the cart is configured to wash cylinder 222a. The cart processor also causes a "draining cycle" indication to be displayed on the cart touch screen 375.

The station processor 372 then activates drain pump 334 of the station. With reference to FIG. 16, waste liquid from cylinder 222a travels through fluid passage 274a (see also FIG. 14) to waste valve 254 and then through fluid passage 256 (see also FIG. 10) and line 386 to the receptacle 259. With reference to FIG. 17, the waste liquid then travels through coupler 334 through station line 342, through drain pump 344 and then to sewer connection 348 where it is disposed.

Venting is provided to cylinder 222a via line 387, fluid passage 282a (see also FIG. 14) and vent valve 258. As illustrated in FIG. 16, line 387 communicates with a vent port in the lid of cylinder 222a. Vent valve 258 communicates with collector 284 via fluid passage 260 (see also FIG. 10) and line 389.

When the liquid level transducer 380a (FIG. 16) detects that there is no more liquid waste in the cylinder 222a, the cart processor causes a "flushing cycle" indication to be displayed on the cart touch screen 376 and sends a signal to the station processor 372 (FIG. 17) indicating that the flushing cycle should begin. With reference to FIG. 17, the station processor activates flushing pump 356 so that a mixture of bleach and enzyme are provided to the chemical injection fitting 358. This mixture is combined with water in the chemical injection fitting 358 so that the resulting disinfecting solution is supplied via line 340 to the coupler 334.

With reference to FIG. 16, the disinfecting solution travels from the coupler 334 through the receptacle 259, line 388 and fluid passage 252 (see also FIG. 10) to wash valve 250. The disinfecting solution then travels through fluid passage 268a (see also FIG. 14) to rotating nozzle 392a so that the interior of cylinder 222a is flushed with the disinfecting solution. The disinfecting solution combined with the liquid waste remaining in the cylinder 222a travels out of the cylinder through fluid passage 274a and, as during the draining cycle, is directed through the waste valve 254, fluid passage 256, line 386, cart receptacle 259, station coupler 334, line 342, drain pump 344 and final to sewer connection 348 for disposal.

After a period of time, the station flushing pump 356 is deactivated by the station processor while the station drain pump continues to run so that all of the liquid in cylinder 222a drains. When the liquid level transducer 380a indicates that cylinder 222a is empty, the flushing pump is again activated so that the flushing cycle is repeated. The station and cart processors keep track of the number of flushing cycles and preferably two or three flushing cycles are performed. When the last flushing cycle is performed, the "flushing cycle" indication provided on touch screen 376 is extinguished with both the station flushing and drain pumps deactivated.

If the liquid level transducer 380b of the cart detects the presence of waste liquid in cylinder 222b, the cart processor the cart processor energizes electric valve drive motor 296 and reconfigures the cart valves into the configuration indicated in FIG. 18B. The above process is then repeated for cylinder 222b.

In addition to the liquid level transducers 380a and 380b, the cylinders may be optionally be provided with sensors that detect the density or other characteristic of the fluid in the cylinders. As a result, the processor, and thus system, may provide an automatic notification that the operator needs to soak a cylinder for deep cleaning in appropriate situations. The system then provides an automatic soak cycle when the operator accepts the notification. Alternatively, the user may manually configure (via the touch screen 376) the system to provide an extended soaking period to dissolve blood clots and the like.

During the draining and flushing cycles described above, the station processor directs the coupler to maintain the coupler solenoid (176 in FIGS. 4 and 6-8) in an energized state so that it cannot be removed from the cart receptacle.

After the final washing cycle has been completed for either or both of cylinders 222a and 222b, and the cart processor determines there is no more liquid in either cylinder, the cart processor energizes the electric drive motor 296 (FIG. 16) so that the valves 250, 254, 258 and 262 are again placed in the configuration illustrated in FIG. 18C. As described previously, in this configuration, the wash, waste and vent valves 250, 254 and 258 are all closed or "off," however, the short loop valve 262 is open or "on." This causes the cart wash supply line 388 to communicate with the fluid passage 286a (see also FIG. 14) and the inlet of the short loop valve 262. The outlet of the short loop valve 262 communicates with fluid passage 395 (FIGS. 10 and 16) and cart drain line 386. The station drain pump continues to run so that any liquid remaining in the wash line 340 and drain line 342 of the station composite hose is completely drained and routed to the station sewer connection 348. This prevents drips from the coupler 334 when it is disengaged from the station receptacle 259.

As illustrated in FIG. 17, the station features pressure sensor 403 and flow meter 405 in communication with drain line, both of which communicate with the station processor 372. As a result, the processor can detect when the drain pump 344 is functioning and at what flow rate.

The station may optionally use the pressure sensor 403 and flow meter 405 to detect clogs in the drain line. When a clog is detected, the processor may reverse direction of the drain pump 344 to momentarily cause a back flush to help remove the clog automatically.

The station also includes flow meter 406, which detects the flow rate of the bleach and enzyme mixture to the chemical injection fitting 358, and flow meter 408, which detects the flow rate of water to the chemical injection fitting. Both flow meters 406 and 408 communicate with the station processor so that it may adjust the speed of the flushing pump 356 so that the proper solution composition is provided to the cart.

Figure 19:
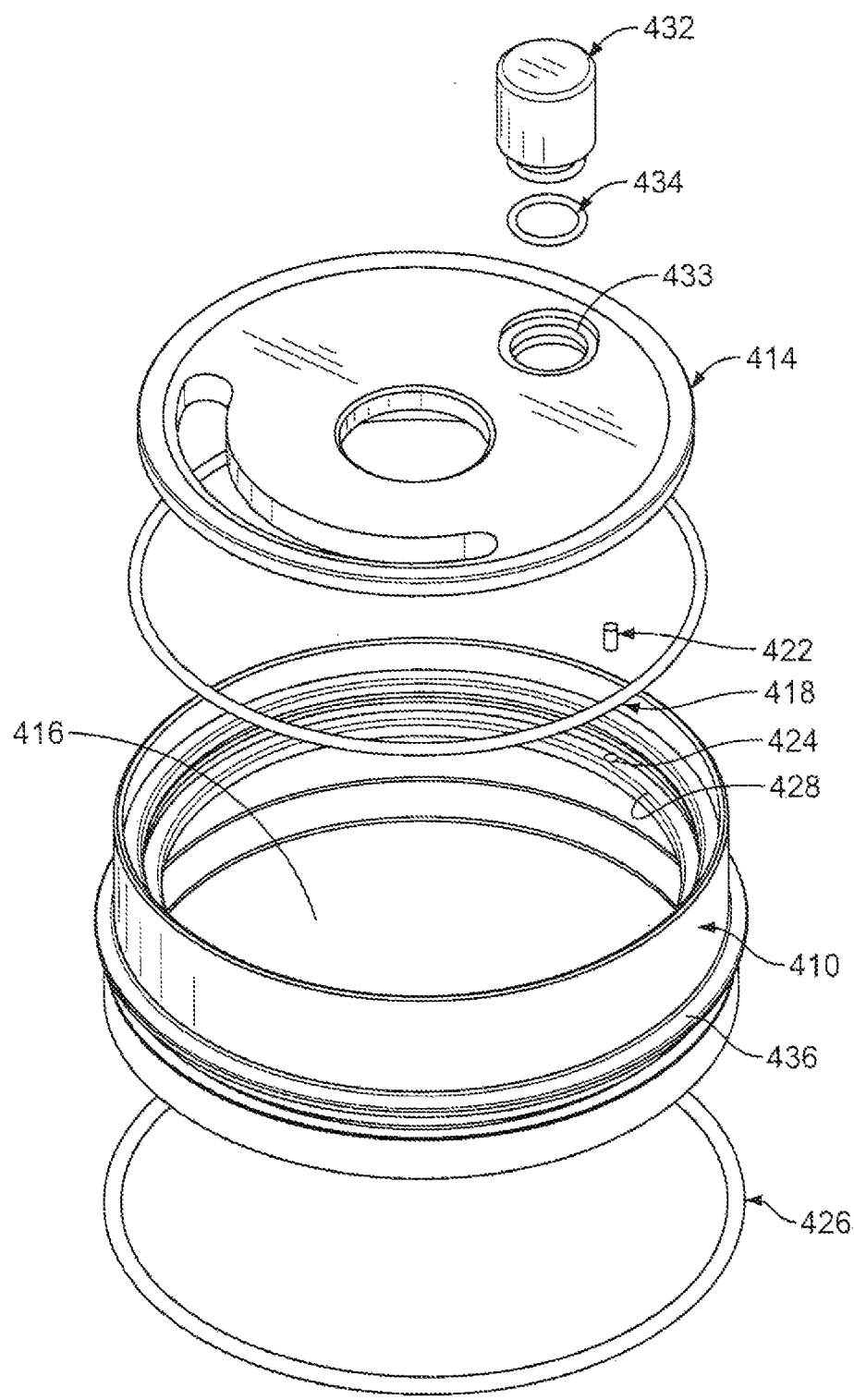
FIG. 19 is an exploded view of the cart lid ring assembly.
Figure 20:
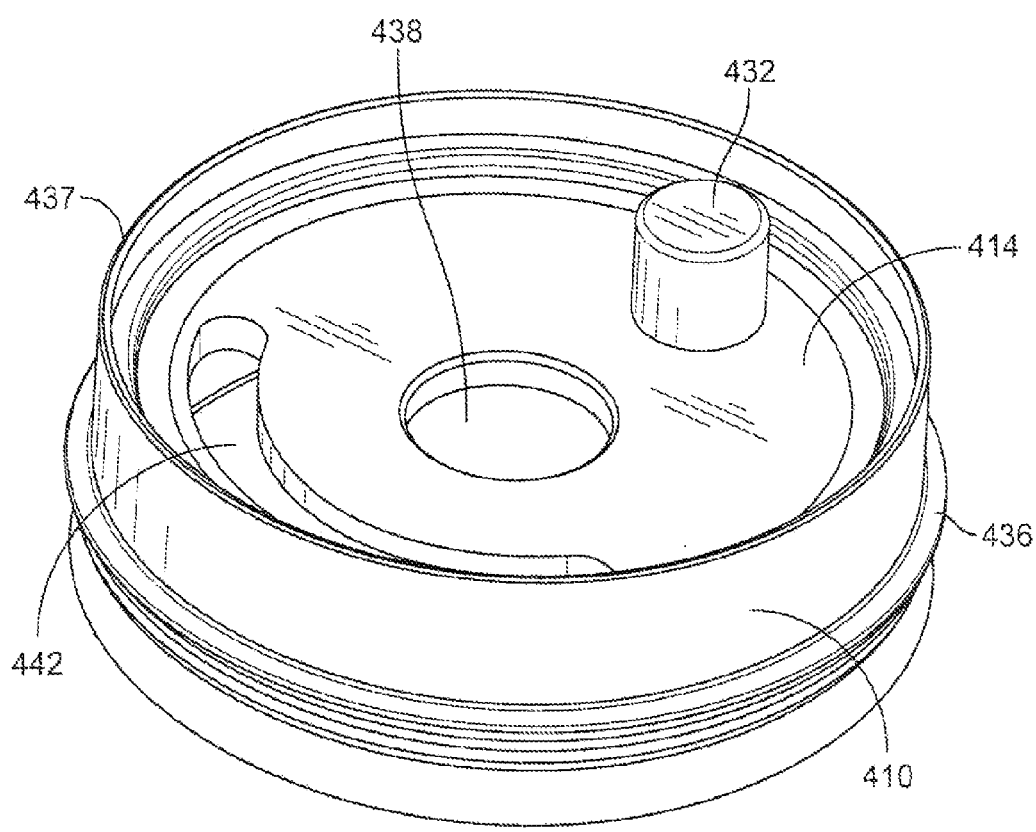
FIG. 20 is an assembled perspective view of the cart lid ring assembly of FIG. 19.

As illustrated in FIG. 10, lid 261a engages a cart lid ring 410. Lid 261b (FIG. 9) engages a similar cart lid ring. As illustrated in FIGS. 19 and 20, the cart lid ring 410 is part of a cart lid ring assembly, one each of which, with reference to FIG. 11, is mounted within the circular openings 412a and 412b formed in cart top plate 224. As illustrated in FIG. 19, a lid alignment member 414 is positioned within the central opening 416 of the cart lid ring 410, with O-ring 418 positioned there between for sealing. A dowel pin 422 is positioned within a bore 424 formed in the cart lid ring 410 and engages a corresponding bore formed in lid alignment member 414. A second O-ring 426 is positioned between the top of a fluid collection cylinder (such as 222a or 222b in FIG. 9) and an interior circumferential ledge 428 formed within the cart lid ring 410. A lid alignment spud 432 is secured to the lid alignment member 414 by threaded engagement with aperture 433. An O-ring 434 is positioned there between.

The assembled cart lid ring assembly is illustrated in FIG. 20. The cart lid ring 410 includes an exterior circumferential ledge 436 that engages the top of cart top plate when the cart lid ring assembly is mounted to the cart top plate 224 (FIG. 10). The cart lid ring also includes a circumferential lip 437 that is engaged by the lid. The openings 438 and 442 formed in the lid alignment member 414 permit the ports of the lid to communicate with the interior of the fluid collection cylinder. The lid alignment spud 432 engages the cylinder lid accessory port (128 in FIG. 2) so that the remaining lid ports are aligned with openings 438 and 442. The cylinder lid snaps onto the top edge 444 of the cart lid ring, as illustrated in FIG. 10. The top edge or other portion of the cart lid ring 410 or lid alignment member 414 may be provided with an alternative lid alignment and/or locking arrangement which may or may not require a corresponding structure on the cylinder lid.

The cart lid ring 410 and lid alignment member 414 are both preferably constructed of aluminum or stainless steel, but other materials may alternatively be used.

In addition to holding the lid, the cart lid ring assembly prevents splash back and is an accessible opening if needed to service or clean the inside of the cylinder. In addition, the lid alignment member 414 provides a support for the lid's main body so that the lid is not supported solely around the circumferential edge of the lid. This prevents any lid failure due to the lid imploding into the cylinder.

Figure 21:
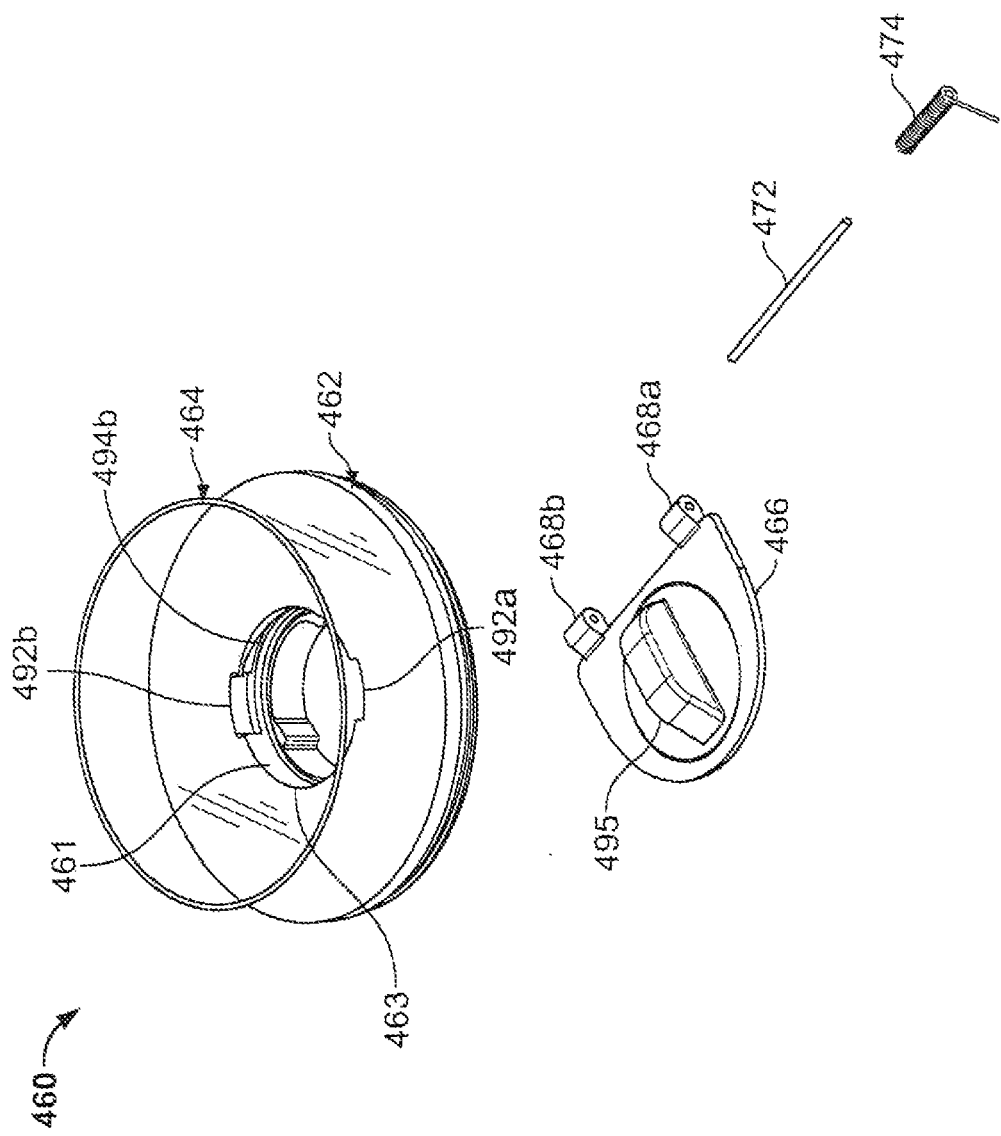
FIG. 21 is an exploded view of a lid insert assembly in an alternative embodiment of the cart.
Figure 22:
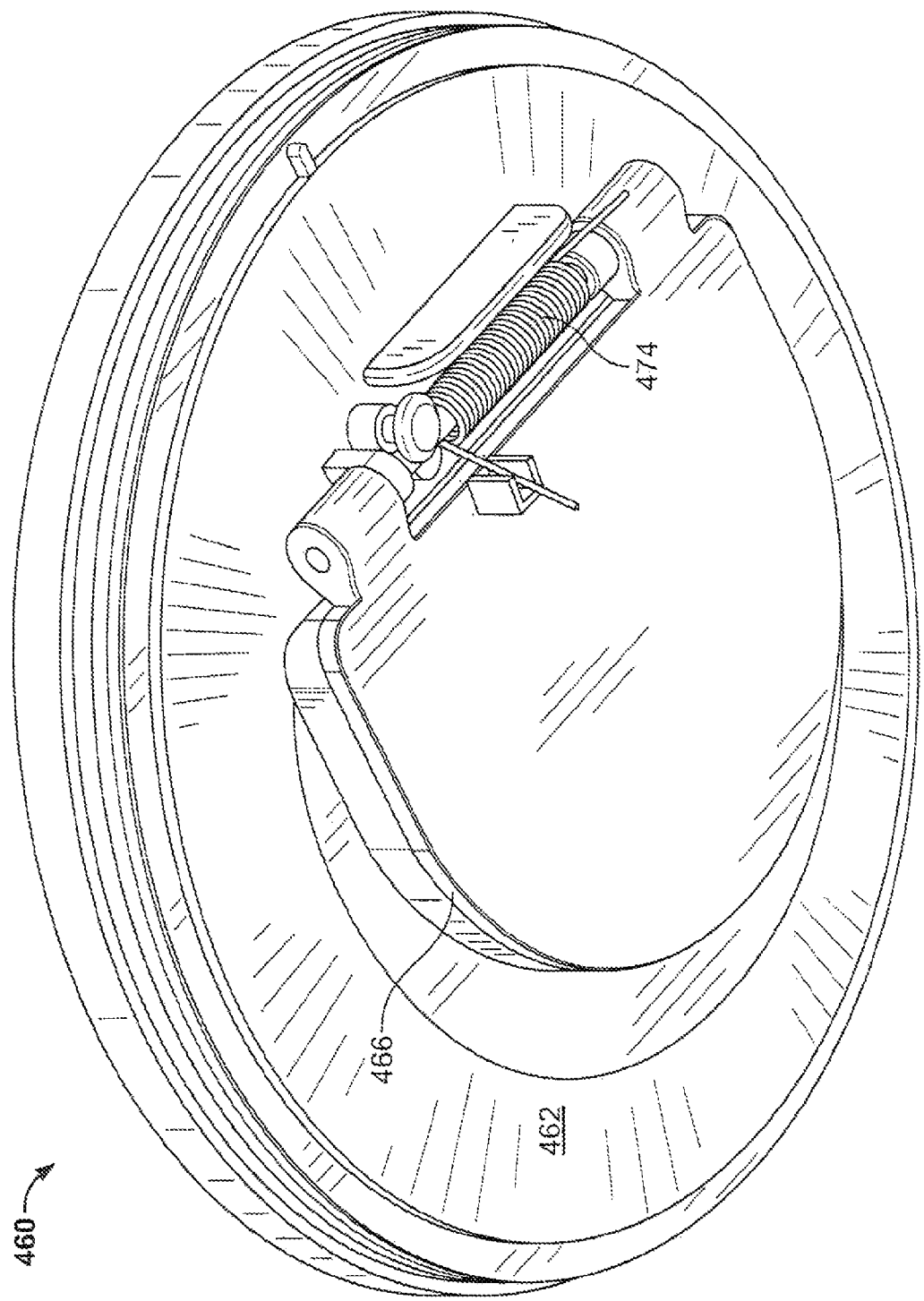
FIG. 22 is an assembled perspective view of the lid insert assembly of FIG. 21 in a closed configuration.
Figure 23:
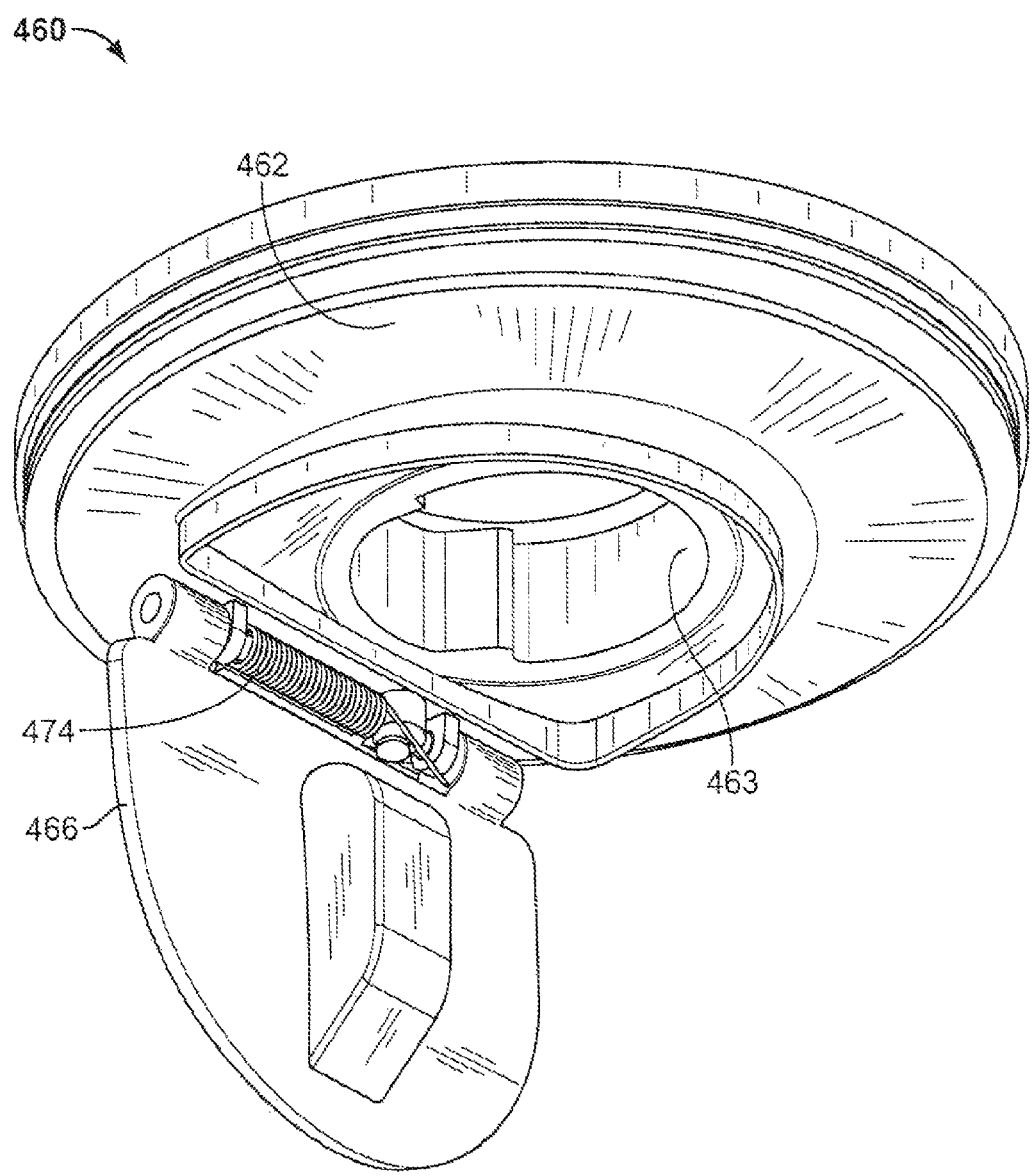
FIG. 23 is a perspective view of the lid insert assembly of FIG. 22 in an open configuration.

In an alternative embodiment of the cart, the lid alignment member 414 of FIGS. 19 and 20 may be replaced by the lid insert assembly, indicated in general at 460 in FIGS. 21-23. As illustrated in FIG. 21, the lid insert assembly includes an insert 462 and an O-ring 464 that is positioned between the insert 462 and the cart lid ring 410 (FIG. 19). The insert 462 includes a central aperture 463. A flap 466 is attached to the bottom of the insert 462 via hinge members 468a and 468b and pin 472 A torsion spring 474 urges the flap 466 into the closed configuration, illustrated in FIG. 22, where the central aperture 463 of the insert 462 is covered. The open configuration of the flap 466, against the urging of torsion spring 474, is illustrated in FIG. 23 and leaves the central aperture 463 of the insert 462 uncovered.

Figure 24:
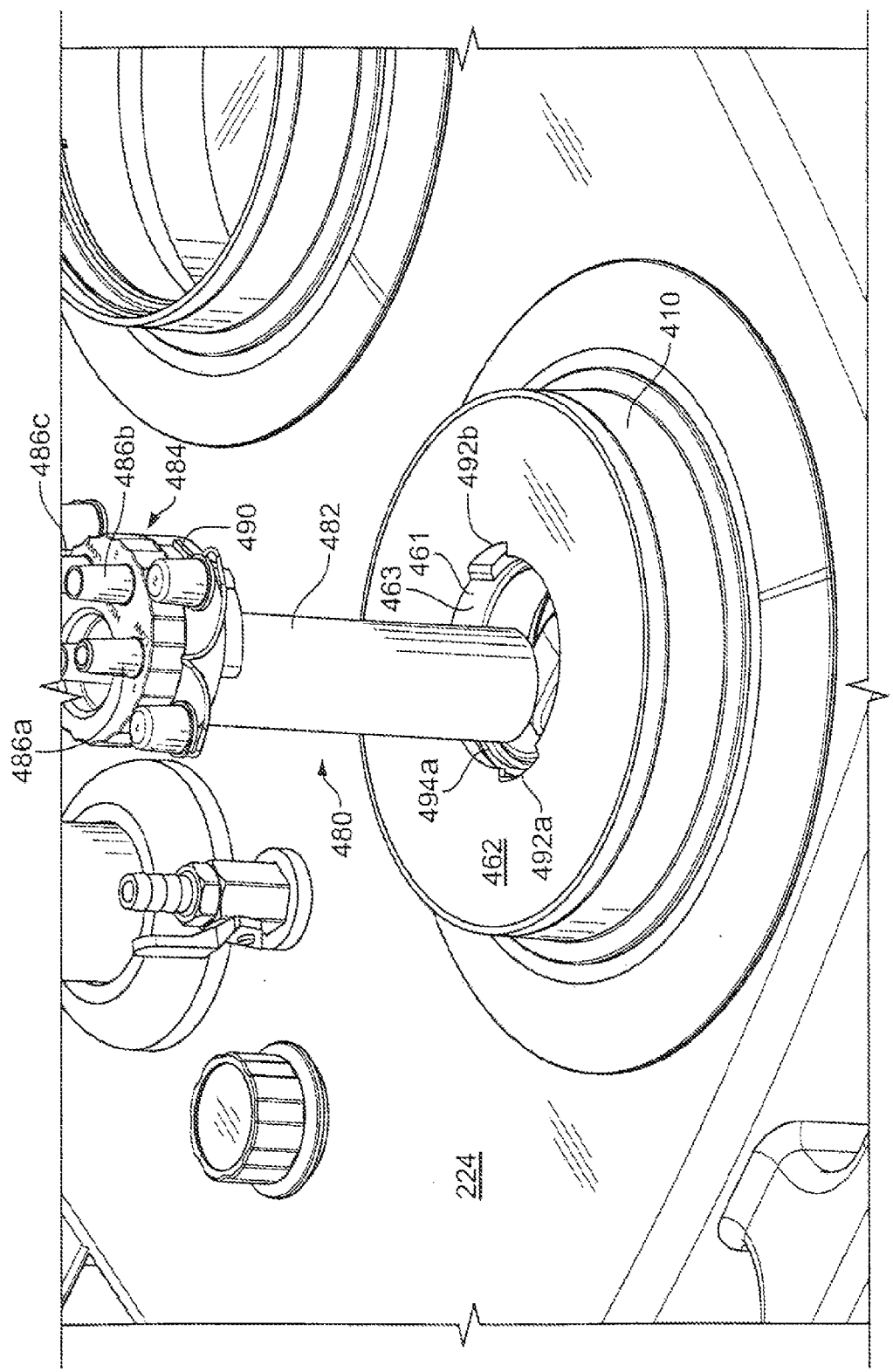
FIG. 24 is a perspective view of the lid insert assembly of FIGS. 21-23 and a portion of the cart of FIG. 9 with a disposable lid being inserted.
Figure 25:
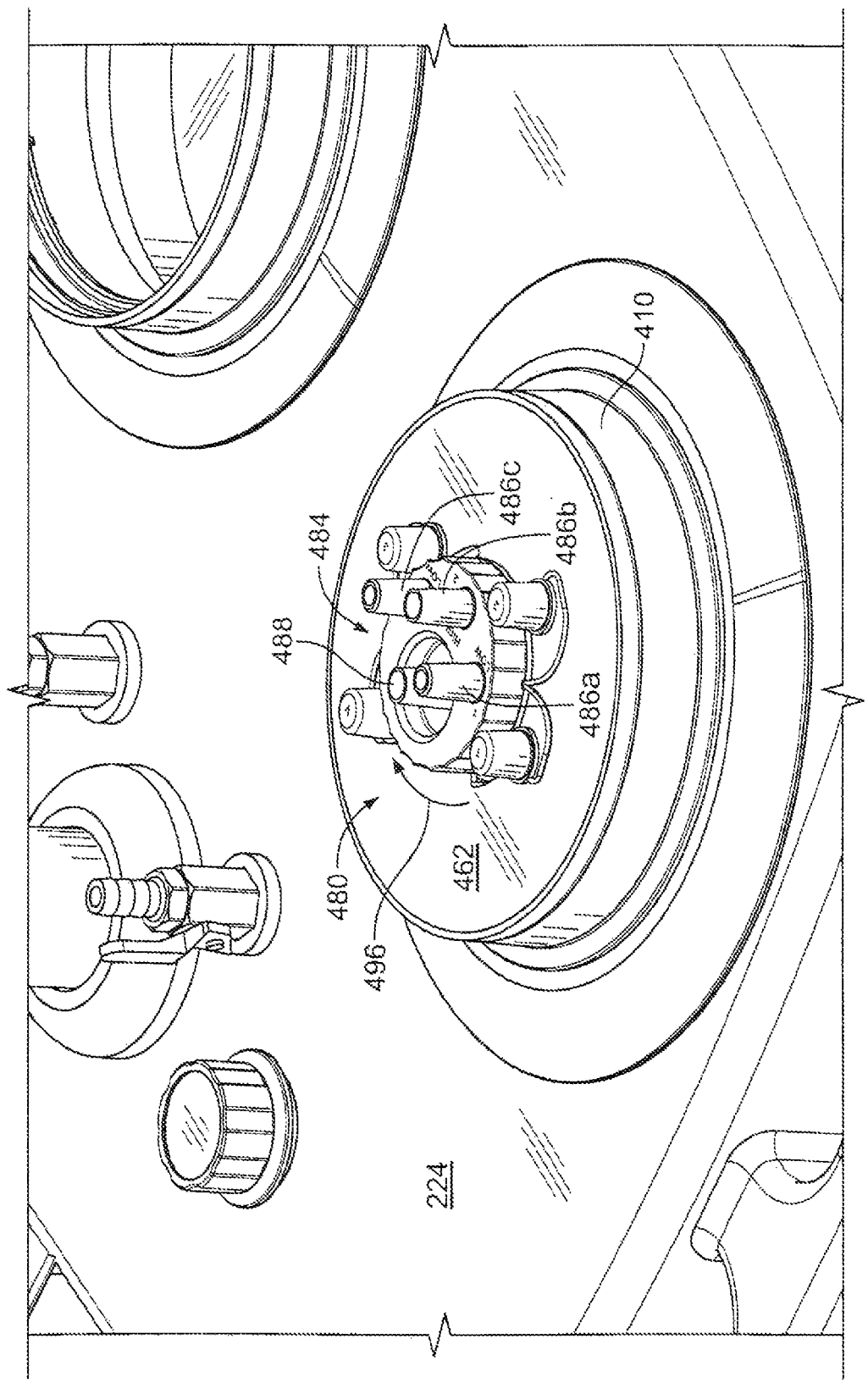
FIG. 25 is a perspective view of the lid insert assembly and portion of the cart of FIG. 24 with the disposable lid fully inserted.

As illustrated in FIGS. 24 and 25, a disposable lid, indicated in general at 480, features a cylindrical portion 482 and a head portion, indicated in general at 484, which features suction ports 486a, 486b and 486c and auxiliary port 488, as well as associated caps. The interior of cylindrical portion is hollow and communicates with the suction and auxiliary ports. The head 484 also features tab 490 and an identical tab (not shown) positioned on the opposite side of head 484.

As illustrated in FIGS. 21 and 24, the wall 461 defining central aperture 462 features notches 492a and 492b which communicate with horizontal slots 494a and 494b, respectively, that are also formed in the wall 461.

To prepare a canister for use in surgery, the cylindrical portion 482 of the disposable lid 480 is moved through the central aperture 463 of the insert 462. As this occurs, the flap 466 of the lid insert assembly swings into the open position illustrated in FIG. 23. This action is aided by arcuate-shaped opening member 495 of FIG. 21, which is engaged by the bottom of the lid cylindrical portion. As the lid is further lowered into the central opening 463, the tabs 490 of the head 484 are aligned with notches 492a and 492b of the insert 462 and the lid 480 is lowered into the positioned illustrated in FIG. 25. The head 484 is the turned, as indicated by arrow 496 of FIG. 25 so that the tabs 490 of the lid move through horizontal slots 494a and 494b of FIGS. 21 and 24. As a result, the disposable lid 480 is secured in place, and suction tubes may be attached to ports 486a-486c.

After surgery is completed, the disposable lid 480 may be removed from the insert 462 by performing the sequence of the above paragraph in reverse order. After the disposable lid is removed from the insert, the flap 466 moves into the closed configuration of FIG. 22. As a result, the contents of the canister cannot splash out or otherwise escape from the canister as the cart is transported.

Figure 26:
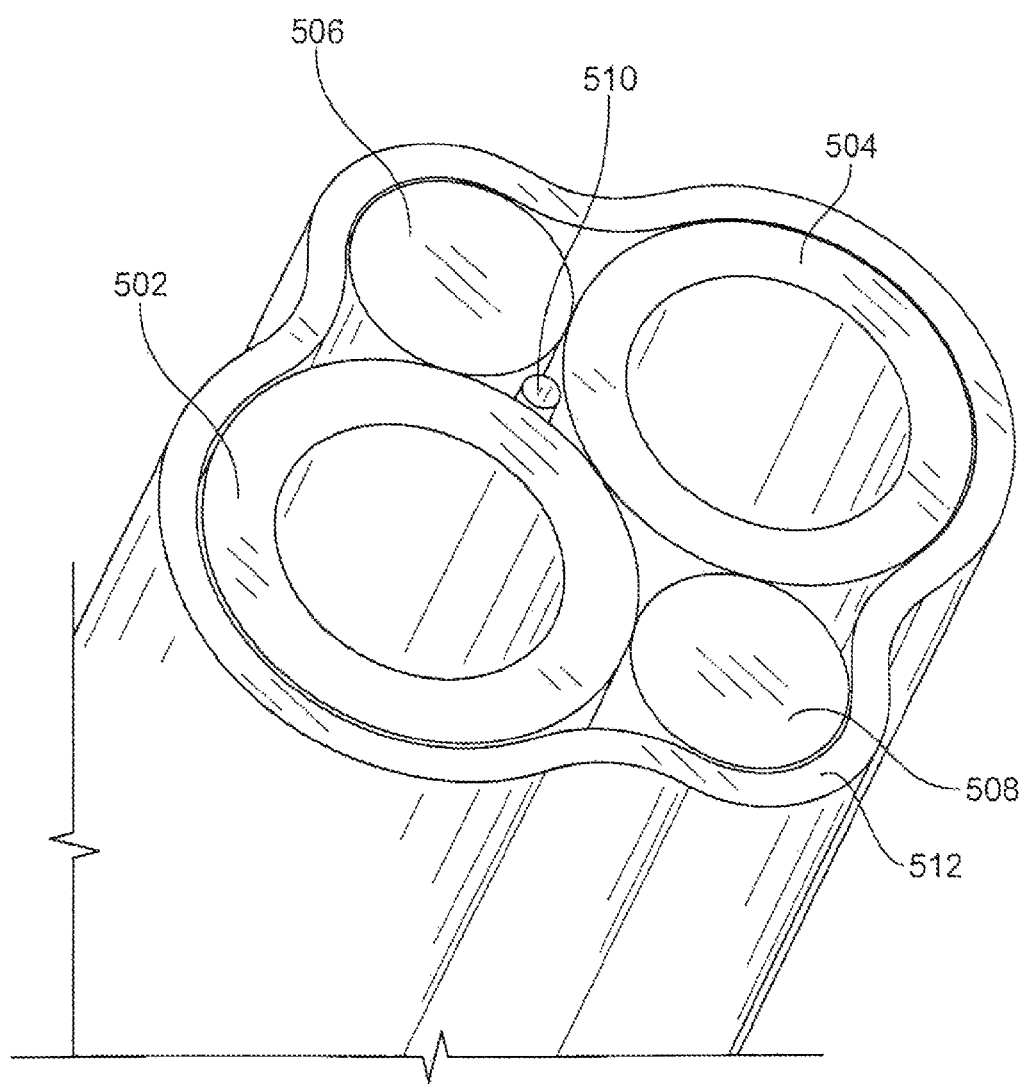
FIG. 26 is a sectional view of an embodiment of the composite hose of the invention.

An alternative embodiment of the composite hose 144 of FIG. 1 is presented in FIG. 26 in cross-section. As illustrated in FIG. 26, the composite hose features PVC hoses 502 and 504, which may be used for the wash supply and drain lines of the evacuation station. The power and data lines of the evacuation station are provided by 10 wire 20 AWG cables 506 and 508. A ground wire 510 is also provided. The hoses 502 and 504, cables 506 and 508 and ground wire 510 are surrounded by an EPDM thermoelastic polymer jacket 512.

Figure 27:
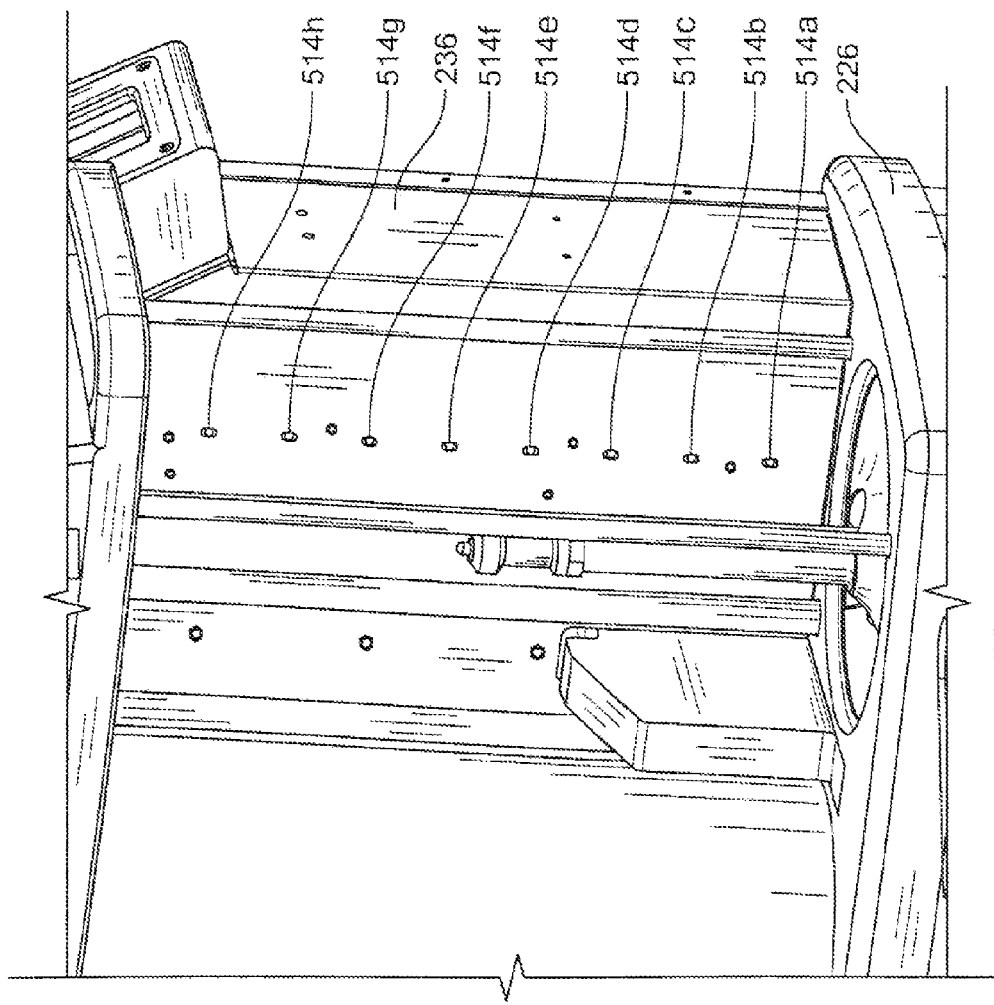
FIG. 27 is a perspective view of a portion of the cart of FIG. 9 with a canister removed to show the canister lighting arrangement.

The cylinders of the cart may optionally feature lighting that is automatically illuminated when either cylinder, or both, is in use during a medical procedure. With reference to FIG. 9, the lighting may be activated by touch screen 376 or may automatically be activated by the cart processor when the cart is in use during surgery. With reference to FIG. 27, the lighting preferably takes the form of multiple light-emitting diodes 514a-514h that extend vertically behind each canister. The illumination allows the liquid level in each canister to be easily monitored by the operator.

Figure 28:
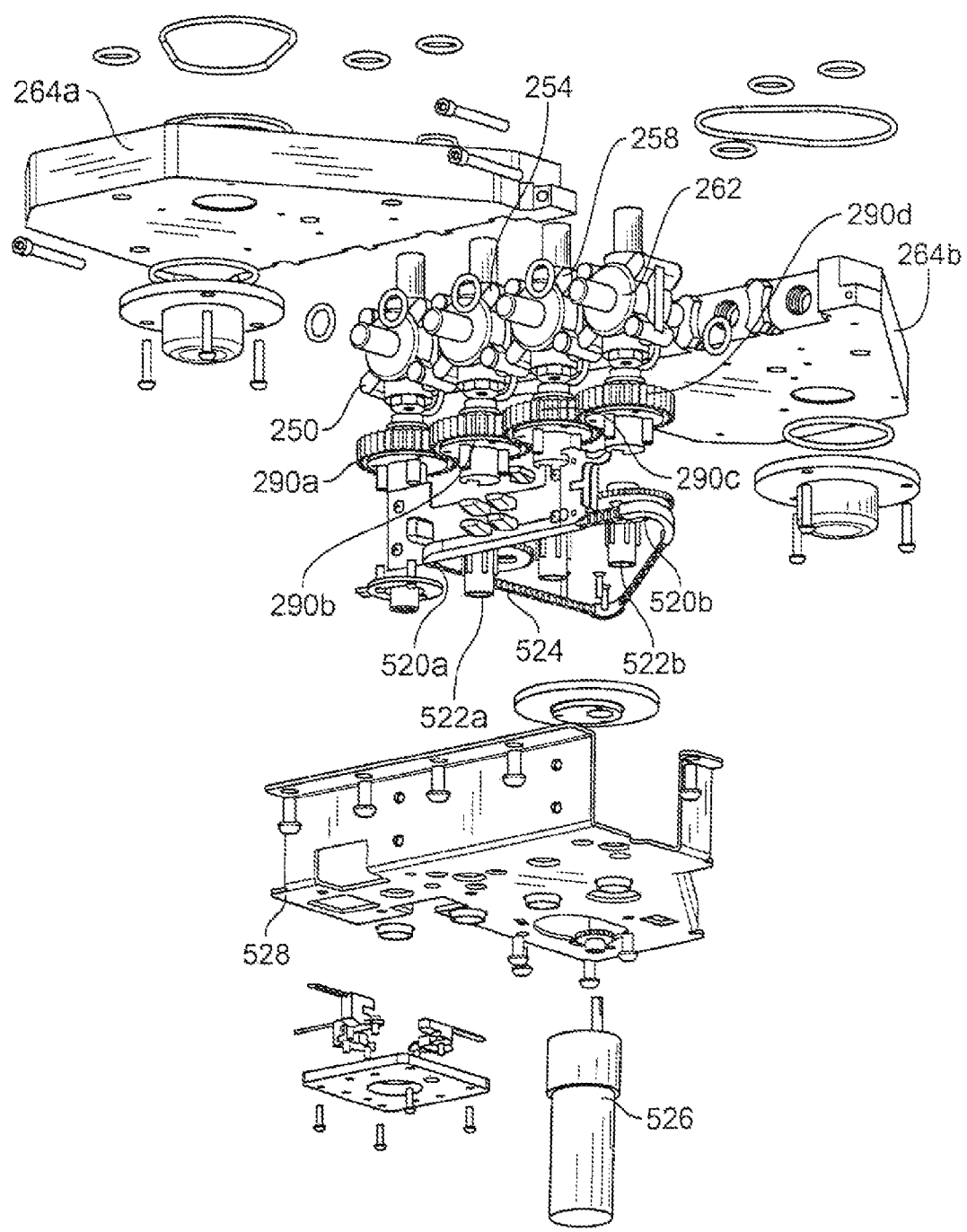
FIG. 28 is an exploded enlarged perspective view of an alternative embodiment of the valve assembly and valve drive system of the cart of FIGS. 9-12.
Figure 29:
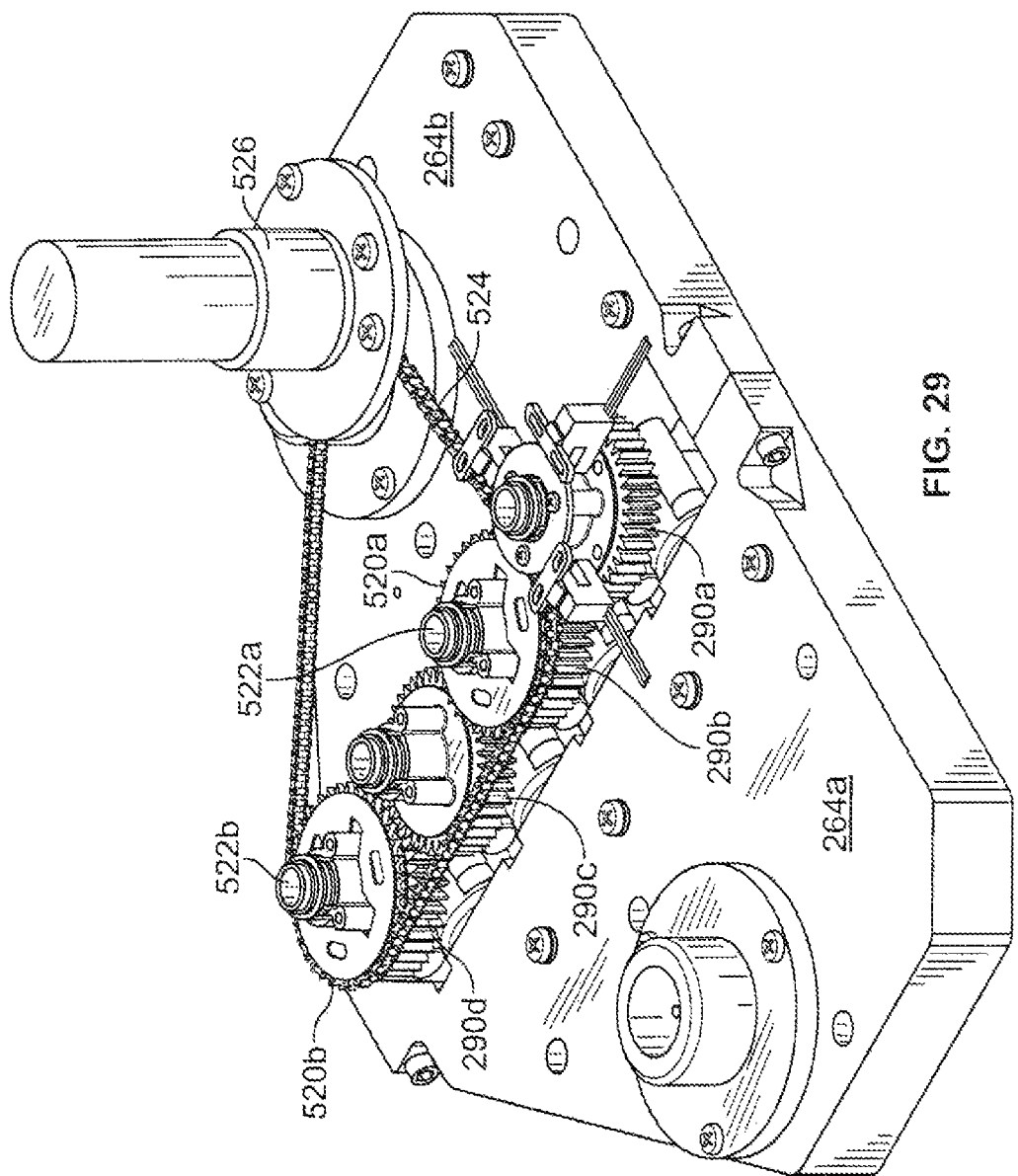
FIG. 29 is a bottom perspective view of the valve assembly and valve drive system of FIG. 28 after assembly but with the drive housing removed.
Figure 30:
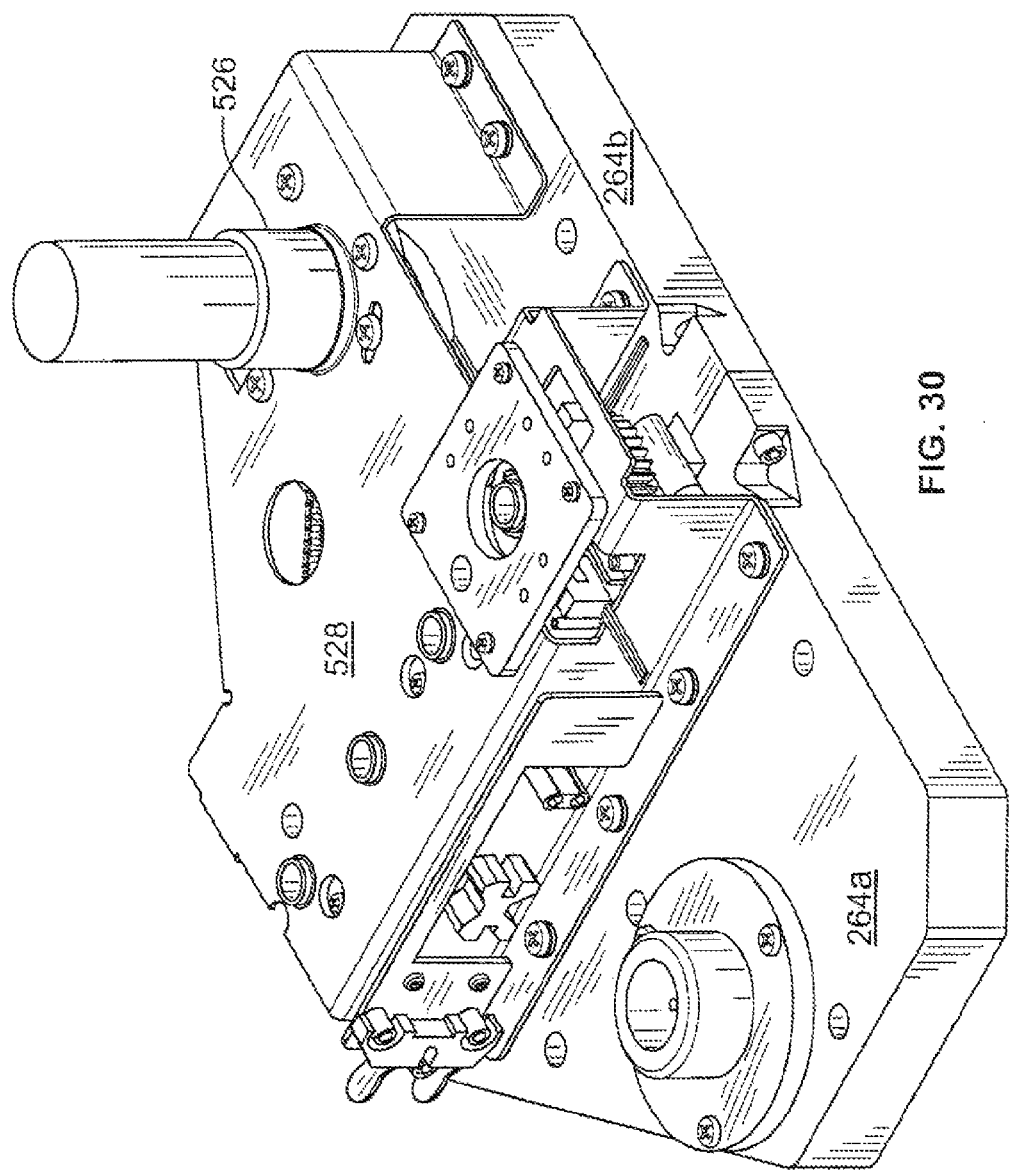
FIG. 30 is a bottom perspective view of the valve assembly and valve drive system of FIG. 29 with the drive housing in place.

As illustrated in FIGS. 28-30, the valve drive system of the cart may include a chain drive in place of the worm gear arrangement of FIG. 12. More specifically, valves 250, 254, 258 and 262 of FIG. 28 are controlled via a valve drive system that includes a gear train featuring gears 290a, 290b, 290c and 290d. As illustrated in FIGS. 28 and 29, a pair of sprockets 520a and 520b are secured to gears 290b and 290d, respectively, by spur gear inserts 522a and 522b. Sprockets 520a and 520b are engaged by a drive chain 524 which is selectively driven by an electric drive motor 526. As a result, the configuration of the valves 250, 254, 258 and 262 may be controlled by activation of the electric drive motor 526. As illustrated in FIGS. 28 and 30, the gear train, sprockets, drive chain and electric drive motor are secured to the manifold blocks 264a and 264b by drive housing 528.

The above system therefore provides a cart that collects fluids in the operating room with an on board vacuum, and also offers automated operation with touch screen menu control. The system also includes a station "coupler" that contains water, waste, and electrical lines in one unit. The coupler automatically engages with a cart when inserted into a "receiver assembly" of the cart and, once engaged with the coupler, the cart automatically cycles through drain, wash, and disinfect cycles. The system is capable of identifying which cart cylinders have fluid in them and drains, washes and disinfects only those cylinders. At the end of the draining, washing and disinfecting, the cart is automatically changed back to operation for the operating room. The system also provides a warning prior to cylinders becoming full during fluid collection in the operation room to allow operator to change to next cylinder if needed.

While embodiments of the invention have been shown and described, it will be apparent to those skilled in the art that changes and modifications may be made therein without departing from the spirit of the invention.

What is claimed is:

1. A lid assembly for a canister comprising:
    a) a lid ring adapted to engage an opening of the canister, said lid ring featuring a central opening and a circumferential lip portion;
    b) a lid alignment member positioned within the central opening of the lid ring, said lid alignment member including a lid alignment spud and a slot;
    c) a lid removably engaging the lip portion of the lid ring, said lid featuring an alignment port and a suction port positioned in the lid so that when the alignment port is engaged by the lid alignment spud of the lid alignment member, the suction port is aligned with the slot of the lid alignment member.

2. The lid assembly of claim 1 wherein the lid is disposable.

3. The lid assembly of claim 2 wherein the lid includes a vacuum port and a filter in communication with the vacuum port.

4. The lid assembly of claim 3 wherein the filter is a hydrophobic filter.

5. The lid assembly of claim 1 further comprising:
    d) a lower O-ring adapted to be positioned between the lid ring and the canister; and
    e) an upper O-ring positioned between the lid ring and the lid alignment member.

6. The lid assembly of claim 1 further comprising a dowel pin positioned between the lid ring and the lid alignment member.

7. The lid assembly of claim 1 wherein the lid ring and the lid alignment member are two separate pieces.

* * * * *